United States Patent
Popp et al.

(10) Patent No.: US 7,259,212 B2
(45) Date of Patent: Aug. 21, 2007

(54) (METH)ACRYLIC ESTERS OF POLYALKOXYLATED TRIMETHYLOLPROPANE

(75) Inventors: Andreas Popp, Birkenheide (DE); Thomas Daniel, Waldsee (DE); Jürgen Schröder, Ludwigshafen (DE); Thomas Jaworek, Kallstadt (DE); Rüdiger Funk, Niedernhausen (DE); Reinhold Schwalm, Wachenheim (DE); Matthias Weismantel, Jossgrund-Oberndorf (DE); Ulrich Riegel, Frankfurt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 127 days.

(21) Appl. No.: 10/516,698

(22) PCT Filed: Jun. 10, 2003

(86) PCT No.: PCT/EP03/06054

§ 371 (c)(1),
(2), (4) Date: Dec. 1, 2004

(87) PCT Pub. No.: WO03/104302

PCT Pub. Date: Dec. 18, 2003

(65) Prior Publication Data

US 2006/0020078 A1 Jan. 26, 2006

(30) Foreign Application Priority Data

Jun. 11, 2002 (DE) ................. 102 25 943
Apr. 3, 2003 (DE) ................. 103 15 336

(51) Int. Cl.
| C08F 2/02 | (2006.01) |
| C08F 2/62 | (2006.01) |
| C08F 1/02 | (2006.01) |
| C08F 1/62 | (2006.01) |

(52) U.S. Cl. ................................. 525/329.7
(58) Field of Classification Search ............... 525/329.7
See application file for complete search history.

(56) References Cited

U.S. PATENT DOCUMENTS

| 3,380,831 A | * | 4/1968 | Cohen et al. ............. 430/288.1 |
| 4,187,383 A | | 2/1980 | Cowherd, III et al. |
| 4,873,299 A | * | 10/1989 | Nowakowsky et al. ....... 526/73 |
| 5,356,754 A | | 10/1994 | Kushi et al. |
| 5,472,617 A | | 12/1995 | Barthold et al. |
| 5,482,649 A | | 1/1996 | Meixner et al. |
| 5,506,324 A | * | 4/1996 | Gartner et al. ......... 526/318.41 |
| 5,648,518 A | | 7/1997 | Ritter et al. |
| 5,661,220 A | * | 8/1997 | Faul et al. .................. 525/384 |
| 5,837,789 A | | 11/1998 | Stockhausen et al. |
| 6,395,830 B1 | | 5/2002 | Jonas et al. |
| 6,673,885 B1 | | 1/2004 | Shibata et al. |

FOREIGN PATENT DOCUMENTS

| DE | 100 54 085 | 5/2002 |
| EP | 0 238 050 | 9/1987 |
| EP | 0 264 841 | 4/1988 |
| EP | 0 777 287 | 6/1997 |
| EP | 0 923 147 | 6/1999 |
| WO | WO93/21237 | 10/1993 |
| WO | WO98/47951 | 10/1998 |
| WO | WO 00/44734 | 8/2000 |
| WO | WO 01/10920 | 2/2001 |
| WO | WO 01/14438 | 3/2001 |
| WO | WO 01/41818 | 6/2001 |
| WO | WO 01/45758 | 6/2001 |
| WO | WO 01/56625 | 8/2001 |

OTHER PUBLICATIONS

H.C. Miller, *Radtech*, 91, 321-324 (1991).

* cited by examiner

*Primary Examiner*—Nathan M. Nutter
(74) *Attorney, Agent, or Firm*—Marshall, Gerstein & Borun LLP

(57) ABSTRACT

The present invention relates to novel (meth)acrylic esters of polyalkoxylated trimethylolpropane of the formula

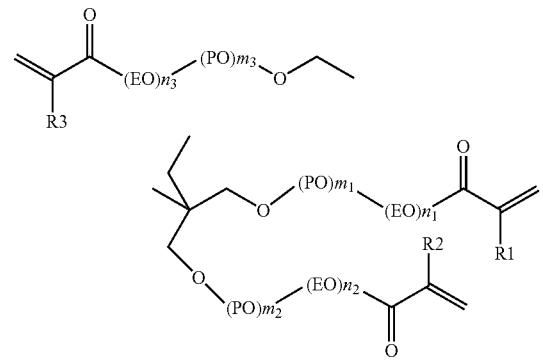

where EO is O—CH2-CH2-
PO is independently at each instance O—CH2-CH(CH3)- or O—CH(CH3)-CH2-
n1, n2 and n3 are independently 4, 5 or 6,
n1+n2+n3 is 14, 15 or 16,
m1, m2 and m3 are independently 1, 2 or 3,
m1+m2+m3 is 4, 5 or 6,
R1, R2 and R3 are independently H or CH3,
a simplified process for preparing these esters and the use of reaction mixtures thus obtainable.

27 Claims, No Drawings

(METH)ACRYLIC ESTERS OF POLYALKOXYLATED TRIMETHYLOLPROPANE

CROSS-REFERENCE TO RELATED APPLICATIONS

This is the U.S. national phase application of International Application No. PCT/EP03/06054, filed Jun. 10, 2003, which claims the benefit of German patent application No. 102 25 943.7, filed Jun. 11, 2002, and German patent application No. 103 15 336.5, filed Apr. 3, 2003.

The present invention relates to novel (meth)acrylic esters of polyalkoxylated trimethylolpropane, a simplified process for preparing these esters and the use of reaction mixtures thus obtainable.

Swellable hydrogel-forming addition polymers, known as superabsorbent polymers or SAPs, are known from the prior art. They are networks of flexible hydrophilic addition polymers, which can be both ionic and nonionic in nature. They are capable of absorbing and binding aqueous fluids by forming a hydrogel and therefore are preferentially used for manufacturing tampons, diapers, sanitary napkins, incontinence articles, training pants for children, insoles and other hygiene articles for the absorption of body fluids. Superabsorbents are also used in other fields of technology where fluids, especially water or aqueous solutions, are absorbed. These fields include for example storage, packaging, transportation (packaging material for water-sensitive articles, for example flower transportation, shock protection); food sector (transportation of fish, fresh meat; absorption of water, blood in fresh fish/meat packs); medicine (wound plasters, water-absorbent material for burn dressings or for other weeping wounds), cosmetics (carrier material for pharmaceuticals and medicaments, rheumatic plasters, ultrasound gel, cooling gel, cosmetic thickeners, sunscreen); thickeners for oil/water or water/oil emulsions; textiles (gloves, sportswear, moisture regulation in textiles, shoe inserts); chemical process industry applications (catalyst for organic reactions, immobilization of large functional molecules (enzymes), adhesive for agglomerations, heat storage media, filtration aids, hydrophilic component in polymer laminates, dispersants, liquefiers); building and construction, installation (powder injection molding, clay-based renders, vibration-inhibiting medium, assistants in relation to tunneling in water-rich ground, cable sheathing); water treatment, waste treatment, water removal (deicers, reusable sandbags); cleaning; agriculture industry (irrigation, retention of meltwater and dew precipitates, composting additive, protection of forests against fungal and insect infestation, delayed release of active ingredients to plants); fire protection (flying sparks)(covering houses or house walls with SAP gel, since water has a very high heat capacity, ignition can be prevented; spraying of SAP gel in the case of fires such as for example forest fires); coextrusion agent in thermoplastic polymers (hydrophilicization of multilayer films); production of films and thermoplastic moldings capable of absorbing water (for example agricultural films capable of storing rain and dew water); SAP-containing films for keeping fresh fruit and vegetables which can be packed in moist films; the SAP stores water released by the fruit and vegetables without forming condensation droplets and partly reemits the water to the fruit and vegetables, so that neither fouling nor wilting occurs; SAP-polystyrene coextrudates for example for food packs such as meat, fish, poultry, fruit and vegetables; carrier substance in active-ingredient formulations (drugs, crop protection). Within hygiene articles, superabsorbents are generally positioned in an absorbent core which comprises other materials, including fibers (cellulose fibers), which act as a kind of liquid buffer to intermediately store the spontaneously applied liquid insults and are intended to ensure efficient channelization of the body fluids in the absorbent core toward the superabsorbent.

The current trend in diaper design is toward ever thinner constructions having a reduced cellulose fiber content and an increased hydrogel content. The trend toward ever thinner diaper constructions has substantially changed the performance profile required of the water swellable hydrophilic polymers over the years. Whereas at the start of the development of highly absorbent hydrogels it was initially solely the very high swellability on which interest focused, it was subsequently determined that the ability of the superabsorbent to transmit and distribute fluid is also of decisive importance. It has been determined that conventional superabsorbents greatly swell at the surface on wetting with liquid, so that transportation of liquid into the particle interior is substantially compromised or completely prevented. This trait of superabsorbents is known as gel blocking. The greater amount of polymer per unit area in the hygiene article must not cause the swollen polymer to form a barrier layer to subsequent fluid. A product having good transportation properties will ensure optimal utilization of the entire hygiene article. This prevents the phenomenon of gel blocking, which in the extreme case will cause the hygiene article to leak. Fluid transmission and distribution is thus of decisive importance with regard to the initial absorption of body fluids.

Good transportation properties are possessed for example by hydrogels having high gel strength in the swollen state. Gels lacking in strength are deformable under an applied pressure, for example pressure due to the bodyweight of the wearer of the hygiene article, and clog the pores in the SAP/cellulose fiber absorbent and so prevent continued absorption of fluid. Enhanced gel strength is generally obtained through a higher degree of crosslinking, although this reduces retention performance of the product. An elegant way to enhance gel strength is surface postcrosslinking. In this process, dried superabsorbents having an average crosslink density are subjected to an additional crosslinking step. Surface postcrosslinking increases the crosslink density in the sheath of the superabsorbent particle, whereby the absorbency under load is raised to a higher level. Whereas the absorption capacity decreases in the superabsorbent particle sheath, the core has an improved absorption capacity (compared to the sheath) owing to the presence of mobile polymer chains, so that sheath construction ensures improved fluid transmission without occurrence of the gel blocking effect. It is perfectly desirable for the total capacity of the superabsorbent to be occupied not spontaneously but with time delay. Since the hygiene article is generally repeatedly insulted with urine, the absorption capacity of the superabsorbent should sensibly not be exhausted after the first disposition.

Highly swellable hydrophilic hydrogels are especially polymers of (co)polymerized hydrophilic monomers, graft (co)polymers of one or more hydrophilic monomers on a suitable grafting base, crosslinked cellulose or starch ethers, crosslinked carboxymethylcellulose, partially crosslinked polyalkylene oxide or natural products which swell in aqueous fluids, for example guar derivatives. Such hydrogels are used as products which absorb aqueous solutions to produce diapers, tampons, sanitary napkins and other hygiene articles, but also as water-retaining agents in market gardening.

To improve the performance properties, for example Rewet in the diaper and AUL, highly swellable hydrophilic hydrogels are generally surface or gel postcrosslinked. This postcrosslinking is known per se to one skilled in the art and is preferably effected in aqueous gel phase or as surface postcrosslinking of the ground and classified polymer particles.

EP 238050 discloses (as possible internal crosslinkers for superabsorbents) doubly or triply acrylates or methacrylated addition products of ethylene oxide and/or propylene oxide with trimethylolpropane.

Sartomer (Exton, Pa., USA), for example, sells under the indicated trade names trimethylolpropane triacrylate (SR 351), triply monoethoxylated trimethylolpropane triacrylate (SR 454), triply diethoxylated trimethylolpropane triacrylate (SR 499), triply triethoxylated trimethylolpropane triacrylate (SR 502), triply pentaethoxylated trimethylolpropane triacrylate (SR 9035) and altogether 20 mol ethoxylated trimethylolpropane triacrylate (SR 415). Propoxylated trimethylolpropane triacrylates are obtainable under the trade names SR 492 (three times 1 PO per TMP) and CD 501 (three times 2 PO per TMP).

WO 93/21237 discloses (meth)acrylates of alkoxylated polyhydric $C_2$-$C_{10}$ hydrocarbons that are useful as crosslinkers. The trimethylolpropane crosslinkers used correspond to SR 351, SR 454, SR 502, SR 9035 and SR 415. These crosslinkers have 0, 3, 9, 15 or 20 EO units per TMP. WO 93/21237 says it is advantageous to have 3 times 2-7 EO units per TMP, and especially 3 times 4-6 EO units per TMP.

The disadvantage with these compounds is that costly and inconvenient purifying operations are needed for at least partial removal of starting materials and by-products; the crosslinkers used in the reference cited have an acrylic acid content of less than 0.1% by weight.

Ethoxylated trimethylolpropane tri(meth)acrylates are again and again mentioned as internal crosslinkers in the patent literature, although only the TMP derivatives commercially available from Sartomer are used, for example trimethylolpropane triethoxylate triacrylate in WO 98/47951, Sartomer #9035 as highly ethoxylated trimethylolpropane triacrylate (HeTMPTA) in WO 01/41818 and SR 9035 and SR-492 in WO 01/56625.

The production of such higher (meth)acrylic esters by acid-catalyzed esterification of (meth)acrylic acid with the corresponding alcohols in the presence of an inhibitor/inhibitor system and in the presence or absence of a solvent such as benzene, toluene or cyclohexane is common knowledge.

Since the formation of the ester from (meth)acrylic acid and alcohol is known to be based on an equilibrium reaction, it is customary to use one starting material in excess and/or to remove the esterification water formed and/or the target ester from the equilibrium in order that commercial conversions may be obtained.

Therefore, in the production of higher (meth)acrylic esters, it is customary to remove the water of reaction and to use an excess of (meth)acrylic acid.

U.S. Pat. No. 4,187,383 describes an esterification process of (meth)acrylic acid with organic polyols at a reaction temperature of from 20 to 80° C. using an equivalent excess of from 2:1 to 3:1.

The disadvantage of this process is that the low reaction temperature means that the reaction times are up to 35 hours and that excess acid in the reaction mixture is removed by neutralization followed by phase separation.

WO 2001/14438 (Derwent Abstract No. 2001-191644/19) and WO 2001/10920 (Chemical Abstracts 134:163502) describe processes for esterifying (meth)acrylic acid with polyalkylene glycol monoalkyl ethers in a ratio of 3:1-50:1 in the presence of acids and polymerization inhibitors and, after deactivation of the acidic catalyst, copolymerization of the residue of (meth)acrylic ester and (meth)acrylic acid at pH 1.5-3.5, and also the use of said residue as a cement additive.

The disadvantage with these processes is that they are restricted to polyalkylene glycol monoalkyl ethers, that the catalyst has to be deactivated and that such copolymers cannot be used as crosslinkers for hydrogels since they only have one functionality.

It is an object of the present invention to provide further compounds which can be used as free-radical crosslinkers for polymers and especially for superabsorbents and to simplify the process for preparing substances which are useful as free-radical crosslinkers for superabsorbents.

We have found that this object is achieved by an ester F of the formula I

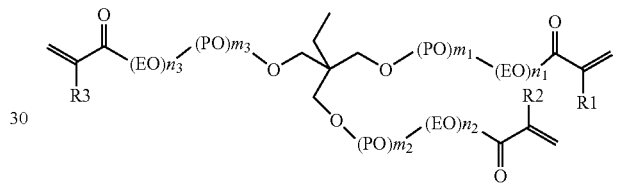

where EO is O—CH2-CH2
PO is independently at each instance O—CH2-CH(CH3)- or O—CH(CH3)-CH2-
n1, n2 and n3 are independently 4, 5 or 6,
n1+n2+n3 is 14, 15 or 16,
m1, m2 and m3 are independently 1, 2 or 3,
m1+m2+m3 is 4, 5 or 6,
R1, R2 and R3 are independently H or CH3.

The EO or PO units have been incorporated in such a way that polyethers are formed and not peroxides.

Preference is given to esters F having the above meanings wherein n1+n2+n3 is 15.

Particular preference is given to esters F having the above meanings wherein n1=n2=n3=5.

Preference is also given to esters F having the above meanings wherein m1+m2+m3 is 5.

Particular preference is also given to esters F having the above meanings wherein m1=m2=2 and m3=1.

Very particular preference is given to esters F wherein R1, R2 and R3 are identical, especially when R1, R2 and R3 are each H.

We have found that the object is further achieved by a process for preparing an ester F of alkoxylated trimethylolpropane with (meth)acrylic acid, comprising the steps of a) reacting alkoxylated trimethylolpropane with (meth) acrylic acid in the presence of at least one esterification catalyst C and of at least one polymerization inhibitor D and optionally also of a water-azeotroping solvent E to form an ester F, b) optionally removing from the reaction mixture some or all of the water formed in a), during and/or after a), f) optionally neutralizing the reaction mixture, h) when a solvent E was used, optionally removing this solvent by distillation, and/or
i) stripping with a gas which is inert under the reaction conditions.

In a preferred embodiment
the molar excess of (meth)acrylic acid to alkoxylated trimethylolpropane is at least 3.15:1 and
the optionally neutralized (meth)acrylic acid present in the reaction mixture after the last step substantially remains in the reaction mixture.

(Meth)acrylic acid in the context of the present invention comprehends methacrylic acid, acrylic acid or mixtures of methacrylic acid and acrylic acid. Acrylic acid is preferred.

When the ester F is desired in pure form, it can be purified by known separation processes.

The molar excess of (meth)acrylic acid to alkoxylated trimethylolpropane is at least 3.15:1, preferably at least 3.3:1, more preferably at least 3.75:1, even more preferably at least 4.5:1 and especially at least 7.5:1.

In a preferred embodiment, (meth)acrylic acid is used in an excess of for example greater than 15:1, preferably greater than 30:1, more preferably greater than 60:1, even more preferably greater than 150:1, especially greater than 225:1 and specifically greater than 300:1.

The esterification products thus obtainable can be used as radical crosslinkers in hydrogels substantially without further purification, specifically without substantial removal of the excess of (meth)acrylic acid and of the esterification catalyst C.

Unless otherwise mentioned, crosslinking as used herein is to be understood as meaning radical crosslinking (gel crosslinking; internal crosslinking; cross-linking together of linear or lightly crosslinked polymer). This crosslinking can take place via free-radical or cationic polymerization mechanisms or other mechanisms, for example Michael addition, esterification or transesterification mechanisms, but is preferably effected by free-radical polymerization.

Hydrogel-forming polymers capable of absorbing aqueous fluids preferably are capable of absorbing at least their own weight, preferably 10 times their own weight of distilled water and they are preferably capable of achieving this absorption even under a pressure of 0.7 psi.

Alkoxylated trimethylolpropane useful for the purposes of the present invention have a structure as in the formula II

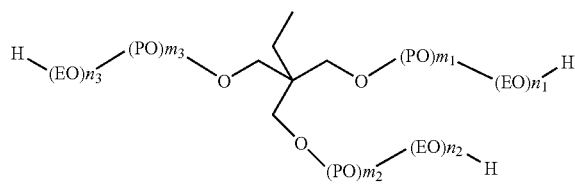

where EO, PO, n1, n2, n3, m1, m2 and m3 are each as defined for the esters.

The reaction of trimethylolpropane with an alkylene oxide is well-known to one skilled in the art. Possible ways of conducting the reaction may be found in Houben-Weyl, Methoden der Organischen Chemie, 4th edition, 1979, Thieme Verlag Stuttgart, editor Heinz Kropf, volume 6/1a, part 1, pages 373 to 385.

An example of a way to prepare compounds of the formula II is to react the trimethylolpropane first with EO and then with PO.

This an be accomplished for example by placing about 77 g of trimethylolpropane with 0.5 g of KOH 45% in water as an initial charge in an autoclave and dewatering the initial charge at 80° C. and reduced pressure (about 20 mbar). The appropriate amount of propylene oxide is then added at 120 to 130° C. and allowed to react at this temperature under elevated pressure. The reaction has ended when no further change in pressure is observed. The reaction mixture is then stirred for a further 30 min at 120° C. The appropriate amount of ethylene oxide is subsequently added at 145 to 155° C. at elevated pressure over a prolonged period and likewise allowed to react. After purging with inert gas and cooling down to 60° C., the catalyst is separated off by addition of sodium pyrophosphate and subsequent filtration.

The viscosity of the polyalcohols which can be used according to the present invention is not subject to any particular requirements bar that they should be readily pumpable to about 80° C., preferably they should have a viscosity below 1000 mPas, preferably below 800 mPas and most preferably below 500 mPas.

Useful esterification catalysts C for the present invention are sulfuric acid, aryl or alkyl sulfonic acids or mixtures thereof. Examples of aryl sulfonic acids are benzenesulfonic acid, para-toluenesulfonic acid and dodecylbenzenesulfonic acid, and examples of alkyl sulfonic acids are methanesulfonic acid, ethanesulfonic acid and trifluoromethanesulfonic acid. Similarly, strongly acidic ion exchangers or zeolites are useful as esterification catalysts. Preference is given to sulfuric acid and ion exchangers.

Useful polymerization inhibitors D for the present invention include for example phenols such as alkylphenols, for example, o-, m- or p-cresol (methylphenol), 2-tert-butyl-4-methylphenol, 6-tert-butyl-2,4-dimethylphenol, 2,6-di-tert-butyl-4-methylphenol, 2-tert-butylphenol, 4-tert-butylphenol, 2,4-di-tert-butylphenol, 2-methyl-4-tert-butylphenol, 4-tert-butyl-2,6-dimethylphenol, or 2,2'-methylenebis(6-tert-butyl-4-methylphenol), 4,4'-oxydiphenol, 3,4-(methylenedioxy)phenol (sesamol), 3,4-dimethylphenol, hydroquinone, pyrocatechol (1,2-dihydroxybenzene), 2-(1'-methylcyclohex-1'-yl)-4,6-dimethylphenol, 2- or 4-(1'-phenyleth-1'-yl)phenol, 2-tert-butyl-6-methylphenol, 2,4,6-tris-tert-butylphenol, 2,6-di-tert-butylphenol, 2,4-di-tert-butylphenol, 4-tert-butylphenol, nonylphenol [11066-49-2], octylphenol [140-66-9], 2,6-dimethylphenol, bisphenol A, bisphenol F, bisphenol B, bisphenol C, bisphenol S, 3,3',5,5'-tetrabromo-bisphenol A, 2,6-di-tert-butyl-p-cresol, Koresin® from BASF AG, methyl 3,5-di-tert-butyl-4-hydroxybenzoate, 4-tert-butylpyrocatechol, 2-hydroxybenzyl alcohol, 2-methoxy-4-methylphenol, 2,3,6-trimethylphenol, 2,4,5-trimethylphenol, 2,4,6-trimethylphenol, 2-isopropylphenol, 4-isopropylphenol, 6-isopropyl-m-cresol, n-octadecyl β-(3,5-di-tert-butyl-4-hydroxyphenyl)propionate, 1,1,3-tris(2-methyl-4-hydroxy-5-tert-butylphenyl)butane, 1,3,5-trimethyl-2,4,6-tris(3,5-di-tert-butyl-4-hydroxybenzyl) benzene, 1,3,5-tris(3,5-di-tert-butyl-4-hydroxybenzyl) isocyanurate, 1,3,5-tris(3,5-di-tert-butyl-4-hydroxyphenyl) propionyloxyethyl isocyanurate, 1,3,5-tris(2,6-dimethyl-3-hydroxy-4-tert-butylbenzyl) isocyanurate or pentaerythritol tetrakis[β-(3,5-di-tert-butyl-4-hydroxyphenyl)propionate], 2,6-di-tert-butyl-4-dimethyl-aminomethylphenol, 6-sec-butyl-2,4-dinitrophenol, Irganox® 565, 1141, 1192, 1222 and 1425 from Ciba Spezialitatenchemie, octadecyl 3-(3',5'-di-tert-butyl-4'-hydroxyphenyl)propionate, hexadecyl 3-(3',5'-di-tert-butyl-4'-hydroxyphenyl)propionate, octyl 3-(3',5'-di-tert-butyl-4'-hydroxyphenyl)propionate, 3-thia-1,5-pentanediol bis[(3',5'-di-tert-4'-hydroxyphenyl)propionate], 4,8-dioxa-1,11-undecanediol bis[(3',5'-di-tert-butyl-4'-hydroxyphenyl)propionate], 4,8-dioxa-1,11-undecanediol bis[(3'-tert-butyl-4'-hydroxy-5'-methylphenyl)propionate], 1,9-nonanediol bis[(3',5'-di-tert-butyl-4'-hydroxyphenyl) propionate], 1,7-heptanediamine bis[3-(3',5'-di-tert-butyl-4'-hydroxyphenyl)propionamide], 1,1-methanediamine bis[3-(3',5'-di-tert-butyl-4'-hydroxyphenyl)propionamide], 3-(3',5'-di-tert-butyl-4'-hydroxyphenyl)propionic acid hydrazide, 3-(3',5'-di-methyl-4'-hydroxyphenyl)propionic acid hydrazide, bis(3-tert-butyl-5-ethyl-2-hydroxyphen-1-yl) methane, bis(3,5-di-tert-butyl-4-hydroxyphen-1-yl)methane, bis[3-(1'-methylcyclohex-1'-yl)-5-methyl-2-hydroxyphen-1-yl]methane, bis(3-tert-butyl-2-hydroxy-5-methylphen-1-yl)methane, 1,1-bis(5-tert-butyl-4-hydroxy-2-methylphen-1-yl)ethane, bis(5-tert-butyl-4-hydroxy-2-methylphen-1-yl) sulfide, bis(3-tert-butyl-2-hydroxy-5-methylphen-1-yl) sulfide, 1,1-bis(3,4-dimethyl-2-hydroxyphen-1-yl)-2-methylpropane, 1,1-bis(5-tert-butyl-3-methyl-2-hydroxyphen-1-yl)butane, 1,3,5-tris-[1'-(3",5"-di-tert-butyl-4"-hydroxyphen-1"-yl)meth-1'-yl]-2,4,6-trimethylbenzene, 1,1,4-tris(5'-tert-butyl-4'-hydroxy-2'-methylphen-1'-yl)butane, aminophenols, for example para-aminophenol, nitrosophenols, for example para-nitrosophenol, p-nitroso-o-cresol, alkoxyphenols, for example 2-methoxyphenol (guajacol, pyrocatechol monomethyl ether), 2-ethoxyphenol, 2-isopropoxyphenol, 4-methoxyphenol (hydroquinone monomethyl ether), mono- or di-tert-butyl-4-methoxyphenol, 3,5-di-tert-butyl-4-hydroxyanisole, 3-hydroxy-4-methoxybenzyl alcohol, 2,5-dimethoxy-4-hydroxybenzyl alcohol (syringa alcohol), 4-hydroxy-3-methoxybenzaldehyde (vanillin), 4-hydroxy-3-ethoxybenzaldehyde (ethylvanillin), 3-hydroxy-4-methoxybenzaldehyde (isovanillin), 1-(4-hydroxy-3-methoxyphenyl)ethanone (acetovanillone), eugenol, dihydroeugenol, isoeugenol, tocopherols, for example α-, β-, γ-, δ- and ε-tocopherol, tocol, α-tocopherolhydroquinone, and also 2,3-dihydro-2,2-dimethyl-7-hydroxybenzofuran (2,2-dimethyl-7-hydroxycoumaran), quinones and hydroquinones such as hydroquinone or hydroquinone monomethyl ether, 2,5-di-tert-butylhydroquinone, 2-methyl-p-hydroquinone, 2,3-dimethylhydroquinone, trimethylhydroquinone, 4-methylpyrocatechol, tert-butylhydroquinone, 3-methylpyrocatechol, benzoquinone, 2-methyl-p-hydroquinone, 2,3-dimethylhydroquinone, trimethylhydroquinone, 3-methylpyrocatechol, 4-methylpyrocatechol, tert-butylhydroquinone, 4-ethoxyphenol, 4-butoxyphenol, hydroquinone monobenzyl ether, p-phenoxyphenol, 2-methylhydroquinone, 2,5-di-tert-butylhydroquinone, tetramethyl-p-benzoquinone, diethyl 1,4-cyclohexanedion-2,5-dicarboxylate, phenyl-p-benzoquinone, 2,5-dimethyl-3-benzyl-p-benzoquinone, 2-isopropyl-5-methyl-p-benzoquinone (thymoquinone), 2,6-diisopropyl-p-benzoquinone, 2,5-dimethyl-3-hydroxy-p-benzoquinone, 2,5-dihydroxy-p-benzoquinone, embelin, tetrahydroxy-p-benzoquinone, 2,5-dimethoxy-1,4-benzoquinone, 2-amino-5-methyl-p-benzoquinone, 2,5-bisphenylamino-1,4-benzoquinone, 5,8-dihydroxy-1,4-naphthoquinone, 2-anilino-1,4-naphthoquinone, anthraquinone, N,N-dimethylindoaniline, N,N-diphenyl-p-benzoquinonediimine, 1,4-benzoquinone dioxime, coerulignone, 3,3'-di-tert-butyl-5,5'-dimethyldiphenoquinone, p-rosolic acid (aurine), 2,6-di-tert-butyl-4-benzylidenebenzoquinone, 2,5-di-tert-amylhydroquinone, nitroxide free radicals such as 4-hydroxy-2,2,6,6-tetramethylpiperidinyloxy free radical, 4-oxo-2,2,6,6-tetramethylpiperidinyloxy free radical, 4-acetoxy-2,2,6,6-tetramethylpiperidinyloxy free radical, 2,2,6,6-tetramethylpiperidinyloxy free radical, 4,4',4"-tris(2,2,6,6-tetramethylpiperidinyloxy) phosphite, 3-oxo-2,2,5,5-tetramethylpyrrolidinyloxy free radical, 1-oxyl-2,2,6,6-tetramethyl-4-methoxypiperidine, 1-oxyl-2,2,6,6-tetramethyl-4-trimethylsilyloxypiperidine, 1-oxyl-2,2,6,6-tetramethylpiperidin-4-yl 2-ethylhexanoate, 1-oxyl-2,2,6,6-tetramethylpiperidin-4-yl stearate, 1-oxyl-2,2,6,6-tetramethylpiperidin-4-yl benzoate, 1-oxyl-2,2,6,6-tetramethylpiperidin-4-yl (4-tert-butyl)benzoate, bis(1-oxyl-2,2,6,6-tetramethylpiperidin-4-yl) succinate, bis(1-oxyl-2,2,6,6-tetramethylpiperidin-4-yl) adipate, bis(1-oxyl-2,2,6,6-tetramethyl-4-piperidinyl) 1,10-decanedioate, bis(1-oxyl-2,2,6,6-tetramethyl-4-piperidinyl) n-butylmalonate, bis(1-oxyl-2,2,6,6-tetramethyl-4-piperidinyl) phthalate, bis(1-oxyl-2,2,6,6-tetramethyl-4-piperidinyl) isophthalate, bis(1-oxyl-2,2,6,6-tetramethyl-4-piperidinyl) terephthalate, bis(1-oxyl-2,2,6,6-tetramethyl-4-piperidinyl) hexahydroterephthalate, N,N'-bis(1-oxyl-2,2,6,6-tetramethyl-4-piperidinyl)adipamide, N-(1-oxyl-2,2,6,6-tetramethyl-4-piperidinyl)caprolactam, N-(1-oxyl-2,2,6,6-tetramethyl-4-piperidinyl)dodecylsuccinimide, 2,4,6-tris[N-butyl-N-(1-oxyl-2,2,6,6-tetramethyl-4-piperidinyl]triazine, N,N'-bis(1-oxyl-2,2,6,6-tetramethyl-4-piperidinyl)-N,N'-bisformyl-1,6-diaminohexane, 4,4'-ethylenebis(1-oxyl-2,2,6,6-tetramethyl-3-piperazinone), aromatic amines such as phenylenediamines, N,N-diphenylamine, N-nitrosodiphenylamine, nitrosodiethylaniline, N,N'-dialkyl-para-phenylenediamine, wherein the alkyl radicals can be the same or different and may each independently contain from 1 to 4 carbon atoms and be straight-chain or branched, for example N,N'-di-iso-butyl-p-phenylenediamine, N,N'-di-iso-propyl-p-phenylenediamine, Irganox 5057 from Ciba Spezialitätenchemie, N,N'-di-iso-butyl-p-phenylenediamine, N,N'-di-iso propyl-p-phenylenediamine, p-phenylenediamine, N-phenyl-p-phenylenediamine, N,N'-diphenyl-p-phenylenediamine, N-isopropyl-N-phenyl-p-phenylenediamine, N,N'-di-sec-butyl-p-phenylenediamine (Kerobit® BPD from BASF AG), N-phenyl-N'-isopropyl-p-phenylenediamine (Vulkanox® 4010 from Bayer AG), N-(1,3-dimethylbutyl)-N'-phenyl-p-phenylenediamine, N-phenyl-2-naphthylamine, iminodibenzyl, N,N'-diphenylbenzidine, N-phenyltetraaniline, acridone, 3-hydroxydiphenylamine, 4-hydroxydiphenylamine, hydroxylamines such as N,N-diethylhydroxylamine, urea derivatives such as urea or thiourea, phosphorus compounds, such as triphenylphosphine, triphenyl phosphite, hypophosphorous acid or triethyl phosphite, sulfur compounds such as diphenyl sulfide, phenothiazine or metal salts, for example copper chloride, copper dithiocarbamate, copper sulfate, copper salicylate, copper acetate, manganese chloride, manganese dithiocarbamate, manganese sulfate, manganese salicylate, manganese acetate, cerium chloride, cerium dithiocarbamate, cerium sulfate, cerium salicylate, cerium acetate, nickel chloride, nickel dithiocarbamate, nickel sulfate, nickel salicylate, nickel acetate, chromium chloride, chromium dithiocarbamate, chromium sulfate, chromium salicylate, chromium acetate or mixtures thereof. Preference is given to the phenols and quinones mentioned, particular preference is given to hydroquinone, hydroquinone monomethyl ether, 2-tert-butyl-4-methylphenol, 6-tert-butyl-2,4-dimethylphenol, 2,6-di-tert-butyl-4-methylphenol, 2,4-di-tert-butylphenol, triphenyl phosphite, hypophosphorous acid, $CuCl_2$ and guajacol, and very particular preference is given to hydroquinone and hydroquinone monomethyl ether.

Particular preference is given to hydroquinone monomethyl ether, hydroquinone and alkylphenols, optionally in combination with triphenyl phosphite and/or hypophosphorous acid.

Very particular preference is given to α-tocopherol (vitamin E), β-tocopherol, γ-tocopherol or δ-tocopherol, optionally in combination with triphenyl phosphite and/or hypophosphorous acid.

Stabilization may be further supported by the presence of an oxygen-containing gas, preferably air or a mixture of air and nitrogen (lean air).

Among the recited stabilizers, preference is given to those which are aerobic, ie those which require the presence of oxygen to fully develop their inhibiting effect.

Useful solvents E for the present invention are particularly solvents which are suitable for azeotropic removal of the water of reaction, if desired, in particular aliphatic, cycloaliphatic and aromatic hydrocarbons or mixtures thereof.

Preference is given to n-pentane, n-hexane, n-heptane, cyclohexane, methylcyclohexane, benzene, toluene or xylene. Particular preference is given to cyclohexane, methylcyclohexane and toluene.

The esterification may be carried out by conventional preparation and/or workup processes for polyhydric alcohols, for example the processes mentioned at the beginning or the processes described in DE-A 199 41 136, DE-A 38 43 843, DE-A 38 43 854, DE-A 199 37 911, DE-A 199 29 258, EP-A 331 845, EP 554 651 or U.S. Pat. No. 4,187,383.

In general, the esterification may be carried out as follows:

The esterification apparatus comprises a stirred reactor, preferably a reactor with circulatory evaporator and an added distillation unit with condenser and phase separation vessel.

The reactor may be for example a reactor with jacketed heating and/or internal heating coils. Preference is given to using a reactor having an external heat exchanger and natural or forced circulation, ie through use of a pump, more preferably natural circulation where circulation is accomplished without mechanical aids.

It will be appreciated that the reaction can also be carried out in a plurality of reaction zones, for example a reactor battery of two to four and preferably two or three reactors.

Suitable circulatory evaporators are known to one skilled in the art and are described for example in R. Billet, Verdampfertechnik, HTB-Verlag, Bibliographisches Institut Mannheim, 1965, 53. Examples of circulatory evaporators are tube-bundle heat exchangers, plate-type heat exchangers, etc.

It will be appreciated that the circulatory system may also include a plurality of heat exchangers.

The distillation unit is of conventional design. It may be a simple distillation unit which if appropriate is equipped with a splash guard or it may be a rectification column. Suitable column internals include in principle all common internals, for example trays, structured packings and/or dumped packings. Preferred trays include bubble trays, sieve trays, valve trays, Thormann trays and/or dual-flow trays, while preferred dumped packings are those of rings, coils, saddles or braids.

In general, from 5 to 20 theoretical plates are sufficient.

The condenser and the separation vessel are of traditional design.

The (meth)acrylic acid and the alkoxylated trimethylolpropane are generally used in the esterification a) in a molar excess as indicated above. The excess used can be up to about 3000:1, if desired.

Useful esterification catalysts C include those recited above.

They are generally used in an amount of 0.1-5% by weight, based on the esterification mixture, preferably 0.5-5%, more preferably 1-4% and most preferably 2-4% by weight.

If necessary, the esterification catalyst can be removed from the reaction mixture with the aid of an ion exchanger. The ion exchanger can be added directly to the reaction mixture and then subsequently filtered off, or the reaction mixture can be passed through an ion exchanger bed.

Preferably, the esterification catalyst is left in the reaction mixture. However, where the catalyst is an ion exchanger, the ion exchanger is preferably removed, for example by filtration.

Stabilization may be further supported by the presence of an oxygen-containing gas, preferably air or a mixture of air and nitrogen (lean air).

This oxygen-containing gas is preferably metered into the bottom region of a column and/or into a circulatory evaporator and/or passed through and/or over the reaction mixture.

The polymerization inhibitor (mixture) D (as indicated above) is used in a total amount of 0.01-1% by weight, based on the esterification mixture, preferably 0.02-0.8% and more preferably 0.05-0.5% by weight.

The polymerization inhibitor (mixture) D may be used for example as an aqueous solution or as a solution in a reactant or product.

b) The water of reaction formed in the course of the reaction can be distilled off during or after the esterification a), in which case this operation can be augmented by a solvent which forms an azeotrope with water.

Useful solvents E for azeotropic removal of the water of reaction, if desired, include the compounds recited above.

The esterification is preferably carried out in the presence of a solvent.

The amount of solvent used is 10-200% by weight, preferably 20-100% by weight and more preferably from 30% to 100% by weight, based on the sum total of alkoxylated trimethylolpropane and (meth)acrylic acid.

However, an operation without entrainer is also conceivable, as described for example in DE-A1 38 43 854, column 2 line 18 to column 4 line 45, but in contradistinction to the cited reference with the abovementioned stabilizers.

When the water in the reaction mixture is not removed via an azeotrope-forming solvent, it may be removed by stripping with an inert gas, preferably an oxygen-containing gas and more preferably air or lean air as described for example in DE-A 38 43 843.

The reaction temperature for the esterification a) is generally in the range from 40 to 160° C., preferably in the range from 60 to 140° C. and more preferably in the range from 80 to 120° C. The temperature may remain constant or rise in the course of the reaction and preferably it is raised in the course of the reaction. In this case, the final temperature of the esterification is 5-30° C. higher than the initial temperature. The temperature of the esterification can be determined and controlled by varying the solvent concentration in the reaction mixture, as described in DE-A 199 41 136 and the German application under file reference 100 63 175.4.

When a solvent is used, it can be distilled out of the reaction mixture through the distillation unit added on top of the reactor.

The distillate may selectively be removed or, after condensation, fed into a phase separation apparatus. The aqueous phase thus obtained is generally removed from the system, while the organic phase can be fed as reflux into the distillation unit and/or passed directly into the reaction zone and/or fed into a circulatory evaporator as described in the German patent application under file reference 100 63 175.4.

When used as reflux, the organic phase can be used as described in DE-A 199 41 136 for controlling the temperature in the esterification.

The esterification a) can be carried out with no pressure, at superatmospheric or reduced pressure and is preferably carried out at atmospheric pressure.

The reaction time is generally in the range from 2 to 20 hours, preferably in the range from 4 to 15 hours and more preferably in the range from 7 to 12 hours.

The order in which the individual reaction components are added is not essential to the present invention. All components can be introduced as a mixed initial charge and subsequently heated, or one or more components may be omitted from or only partly included in the initial charge and added only after the initial charge has been heated up.

The (meth)acrylic acid which can be used is not restricted in its composition and may comprise for example the following components:

| (Meth)acrylic acid | 90–99.9% by weight |
| --- | --- |
| Acetic acid | 0.05–3% by weight |
| Propionic acid | 0.01–1% by weight |
| Diacrylic acid | 0.01–5% by weight |
| Water | 0.05–5% by weight |
| Carbonylics | 0.01–0.3% by weight |
| Inhibitors | 0.01–0.1% by weight |
| Maleic acid or anhydride | 0.001–0.5% by weight |

The crude (meth)acrylic acid used is generally stabilized with 200-600 ppm of phenothiazine or other stabilizers in amounts which permit comparable stabilization. Carbonylics here refers for example to acetone and lower aldehydes, for example formaldehyde, acetaldehyde, crotonaldehyde, acrolein, 2-furfural, 3-furfural and benzaldehyde.

Crude (meth)acrylic acid here refers to the (meth)acrylic acid mixture which is obtained after absorption of the reaction gases of the propane/propene/acrolein or isobutane/isobutene/methacrolein oxidation in an absorbent and subsequent removal of the absorbent, or which is obtained by fractional condensation of the reaction gases.

It is obviously also possible to use pure (meth)acrylic acid, for example of the following purity:

| (Meth)acrylic acid | 99.7–99.99% by weight |
| --- | --- |
| Acetic acid | 50–1000 weight ppm |
| Propionic acid | 10–500 weight ppm |
| Diacrylic acid | 10–500 weight ppm |
| Water | 50–1000 weight ppm |
| Carbonylics | 1–500 weight ppm |
| Inhibitors | 1–300 weight ppm |
| Maleic acid or anhydride | 1–200 weight ppm |

The pure (meth)acrylic acid used is generally stabilized with 100-300 ppm of hydroquinone monomethyl ether or other storage stabilizers in amounts which permit comparable stabilization.

Pure or prepurified (meth)acrylic acid generally refers to (meth)acrylic acid whose purity is at least 99.5% by weight and which is substantially free of aldehydic, other carbonylic and high-boiling components.

The aqueous phase, distilled off during the esterification, of the condensate removed via the added column (if present) may generally contain 0.1-10% by weight of (meth)acrylic acid, and is separated off and removed from the system. The (meth)acrylic acid it contains may preferably be extracted with an extractant, preferably with any solvent used in the esterification, for example with cyclohexane, at from 10 to 40° C. and a ratio of 1:5-30 and preferably 1:10-20 for aqueous phase to extractant, and returned into the esterification.

Circulation may be further supported by passing an inert gas, preferably an oxygen-containing gas, more preferably air or a mixture of air and nitrogen (lean air) into the circulation or through or over the reaction mixture, for example at rates of 0.1-1, preferably 0.2-0.8 and more preferably 0.3-0.7 $m^3/m^3h$, based on the volume of the reaction mixture.

The course of the esterification a) can be monitored by monitoring the amount of water carried out and/or the decrease in the carboxylic acid concentration in the reactor.

The reaction can be ended for example as soon as 90%, preferably at least 95% and more preferably at least 98% of the theoretically expected amount of water has been carried out by the solvent.

The end of the reaction can be detected for example from the fact that substantially no further water of reaction is removed via the entrainer. When (meth)acrylic acid is carried out together with the water of reaction, its fraction is determinable for example by backtitrating an aliquot of the aqueous phase.

The removal of the water of reaction can be dispensed with for example when the (meth)acrylic acid is used in a high stoichiometric excess, for example of at least 4.5:1, preferably at least 7.5:1 and most preferably at least 15:1. In this case, a substantial portion of the amount of water formed will remain in the reaction mixture. Merely that fraction of water is removed from the reaction mixture during or after the reaction which is determined by the volatility at the employed temperature and beyond that no measures are carried out to remove the resulting water of reaction. For instance, at least 10% by weight of the resulting water of reaction can remain in the reaction mixture, preferably at least 20% by weight, more preferably at least 30% by weight, even more preferably at least 40% by weight and most preferably at least 50% by weight.

c) After the end of the esterification the reaction mixture can be conventionally cooled to 10-30° C. and if necessary by addition of a solvent which may be the same as any solvent used for azeotropic removal of water or a different solvent adjusted to any desired target ester concentration.

In a further embodiment, the reaction can be stopped with a suitable diluent G and diluted to a concentration of for example 10-90% by weight, preferably 20-80%, more preferably 20-60%, even more preferably 30-50% and most preferably about 40%, for example in order to reduce the viscosity.

What is important is that a substantially homogeneous solution forms after dilution.

This is preferably accomplished only relatively shortly before use in the production of the hydrogel, for example not more than 24 hours before, preferably not more than 20 hours before, more preferably not more than 12 hours before, even more preferably not more than 6 hours before and most preferably not more than 3 hours before.

The diluent G is selected from the group consisting of water, a mixture of water with one or more organic solvents which are soluble in water in any proportion and a mixture of water with one or more monohydric or polyhydric alcohols, for example methanol and glycerol. The alcohols preferably bear 1, 2 or 3 hydroxyl groups and preferably have from 1 to 10 and especially up to 4 carbon atoms. Preference is given to primary and secondary alcohols.

Preferred alcohols are methanol, ethanol, isopropanol, ethylene glycol, glycerol, 1,2-propanediol and 1,3-propanediol.

d) If necessary, the reaction mixture may be decolorized, for example by treatment with active carbon or metal oxides, for example alumina, silica, magnesium oxide, zirconium oxide, boron oxide or mixtures thereof, in amounts for example of 0.1-50% by weight, preferably from 0.5% to 25% by weight, more preferably 1-10% by weight at temperatures of for example from 10 to 100° C., preferably from 20 to 80° C. and more preferably from 30 to 60° C.

This can be effected by adding the pulverulent or granular decolorizing agent to the reaction mixture and subsequent filtration or by passing the reaction mixture through a bed of the decolorizing agent in the form of any desired suitable moldings.

The decolorizing of the reaction mixture can be effected at any desired stage in the workup process, for example at the stage of the crude reaction mixture or after any prewash, neutralization, wash or solvent removal.

The reaction mixture can further be subjected to a prewash e) and/or a neutralization f) and/or an afterwash g), preferably merely to a neutralization f). If desired, a neutralization f) and a prewash e) can be interchanged in the sequence.

(Meth)acrylic acid, and/or catalyst C can be at least partly recovered from the aqueous phase of the washes e) and g) and/or neutralization f) by acidification and extraction with a solvent and reused.

For a pre- or afterwash e) or g), the reaction mixture is treated in a wash apparatus with a wash liquor, for example water or a 5-30% by weight, preferably 5-20% and more preferably 5-15% by weight sodium chloride, potassium chloride, ammonium chloride, sodium sulfate or ammonium sulfate solution, preferably water or sodium chloride solution.

The ratio of reaction mixture to wash liquor is generally in the range from 1:0.1 to 1:1, preferably in the range from 1:0.2 to 1:0.8 and more preferably in the range from 1:0.3 to 1:0.7.

The wash or neutralization can be carried out for example in a stirred container or in other conventional apparatuses for example in a column or a mixer-settler apparatus.

In terms of process engineering, any wash or neutralization in the process according to the present invention can be carried out using conventional extraction and washing processes and apparatuses, for example those described in Ullmann's Encyclopedia of Industrial Chemistry, 6th ed, 1999 Electronic Release, Chapter: Liquid—Liquid Extraction—Apparatus. For example, the choice may be for single- or multi-staged, preferably single-staged, extractions, and also for these in cocurrent or countercurrent mode and preferably in countercurrent mode.

Preference is given to using sieve tray columns, arrangedly or randomly packed columns, stirred vessels or mixer-settler apparatuses and also pulsed columns or columns having rotating internals.

The prewash e) is preferably used whenever metal salts and preferably copper or copper salts are (concomitantly) used as inhibitors.

An afterwash g) may be preferable to remove traces of base or salt traces from the reaction mixture neutralized in f).

By way of neutralization f), the reaction mixture which may have been prewashed and which may still contain small amounts of catalyst and the main amount of excess (meth) acrylic acid can be neutralized with a 5-25%, preferably 5-20% and more preferably 5-15% by weight aqueous solution of a base, for example alkali metal or alkaline earth metal oxides, hydroxides, carbonates or bicarbonates, preferably aqueous sodium hydroxide solution, aqueous potassium hydroxide solution, sodium bicarbonate, sodium carbonate, potassium bicarbonate, calcium hydroxide, milk of lime, ammonia gas, ammonia water or potassium carbonate, to which solution 5-15% by weight of sodium chloride, potassium chloride, ammonium chloride or ammonium sulfate may have been added, if desired, more preferably with aqueous sodium hydroxide solution or aqueous sodium hydroxide-sodium chloride solution. The degree of neutralization is preferably in the range from 5 to 60 mol %, preferably in the range from 10 to 40 mol %, more preferably in the range from 20 to 30 mol %, based on the acid-functional monomers. This neutralization can take place before and/or during the polymerization, preferably before the polymerization.

The base is added in such a way that the temperature in the apparatus does not rise above 60° C. and is preferably in the range from 20 to 35° C., and the pH is 4-13. The heat of neutralization is preferably removed by cooling the vessel with the aid of internal cooling coils or via jacketed cooling.

The ratio of reaction mixture to neutralizing liquor is generally in the range from 1:0.1 to 1:1, preferably in the range from 1:0.2 to 1:0.8 and more preferably in the range from 1:0.3 to 1:0.7.

With regard to the apparatus, the above statements apply.

h) When a solvent is present in the reaction mixture, it may be substantially removed by distillation. Preferably, any solvent present is removed from the reaction mixture after washing and/or neutralization, but if desired this may also be done prior to the wash or neutralization.

For this, the reaction mixture is admixed with an amount of storage stabilizer, preferably hydroquinone monomethyl ether, such that, after removal of the solvent, 100-500, preferably 200-500 and more preferably 200-400 ppm thereof are present in the target ester (residue).

The distillative removal of the main amount of solvent is effected for example in a stirred tank with jacketed heating and/or internal heating coils under reduced pressure, for example at 20-700 mbar, preferably 30-500 mbar and more preferably 50-150 mbar and 40-80° C.

It will be appreciated that the distillation can also be accomplished in a falling-film or thin-film evaporator. For this, the reaction mixture is recirculated, preferably two or more times, through the apparatus under reduced pressure, for example at 20-700 mbar, preferably 30-500 mbar and more preferably 50-150 mbar and 40-80° C.

An inert gas, preferably an oxygen-containing gas, more preferably air or a mixture of air and nitrogen (lean air) may preferably be introduced into the distillation apparatus, for example 0.1-1, preferably 0.2-0.8 and more preferably 0.3-0.7 $m^3/m^3h$, based on the volume of the reaction mixture.

The residual solvent content of the residue is generally below 5% by weight, preferably 0.5-5% and more preferably 1-3% by weight after the distillation.

The removed solvent is condensed and preferably reused.

If necessary, a solvent stripping operation i) can be carried out in addition to or in lieu of the distillation.

For this, the target ester, which still contains small amounts of solvent, is heated to 50-90° C. and preferably 80-90° C. and the remaining amounts of solvent are removed with a suitable gas in a suitable apparatus. There are circumstances where a vacuum can be applied in support, if desired.

Examples of useful apparatus include columns of conventional design which contain conventional internals, for example trays, dumped packing or structured packing, preferably dumped packing. Useful column internals include in principle all common internals, for example trays, arranged packing and/or random packing. Preferred trays include bubble trays, sieve trays, valve trays, Thormann trays and/or dual-flow trays, while preferred dumped packings are those of rings, coils, saddles, Raschig, Intos or Pall rings, barrel or Intalox saddles, Top-Pak, etc or braids.

Another possibility here is a falling-film, thin-film or wipe-film evaporator, for example a Luwa, Rotafilm or Sambay evaporator, which may be splash-guarded with a demister for example.

Useful gases include gases which are inert under the stripping conditions, preferably oxygen-containing gases, more preferably air or mixtures of air and nitrogen (lean air) or water vapor, especially such gases which have been preheated to 50-100° C.

The stripping gas rate is for example in the range from 5 to 20, more preferably in the range from 10 to 20 and most preferably in the range from 10 to 15 m$^3$/m$^3$h, based on the volume of the reaction mixture.

If necessary, the ester can be subjected to a filtration j) at any stage of the workup process, preferably after washing/neutralization and any effected solvent removal, in order that precipitated traces of salts and any decolorizing agent may be removed.

In a conceivable embodiment, the esterification a) of alkoxylated trimethylolpropane with (meth)acrylic acid in the presence of at least one esterification catalyst C and of at least one polymerization inhibitor D is carried out in a molar excess of at least 15:1, as indicated above, without a solvent capable of forming an azeotrope with water.

In a preferred embodiment the excess (meth)acrylic acid is preferably substantially not removed, ie only that fraction of (meth)acrylic acid is removed from the reaction mixture that is determined by the volatility at the employed temperature, and beyond that no measures are carried out to remove the carboxylic acid, for example no distillative, rectificative, extractive (washing for example), absorptive (for example passing through activated carbon or through ion exchangers) and/or chemical steps such as scavenging of the carboxylic acid with epoxides are carried out.

The extent to which the (meth)acrylic acid in the reaction mixture is removed from it is preferably not more than 75% by weight, more preferably not more than 50% by weight, even more preferably not more than 25% by weight, especially not more than 10% by weight and most preferably not more than 5% by weight, based on the (meth)acrylic acid in the reaction mixture after the reaction has ended. In a particularly preferred embodiment, stage b) can be omitted, so that only the fraction of water of reaction and (meth)acrylic acid is removed from the reaction mixture that is determined by the volatility at the employed temperature. This can preferably be prevented by substantially complete condensation.

Furthermore, the esterification catalyst C used is likewise substantially left in the reaction mixture.

The DIN EN 3682 acid number of the reaction mixture thus obtainable is preferably at least 25 mg of KOH/g of reaction mixture, more preferably in the range from 25 to 80 and most preferably in the range from 25 to 50 mg of KOH/g.

Any pre- or afterwash e) or g) is preferably omitted; merely a filtration step j) can be sensible.

The reaction mixture can subsequently be diluted in step c), in which case it is preferably converted within 6 hours and more preferably within 3 hours to the hydrogel. It may preferably be neutralized in a step f).

The order of the steps c), j) and f) is arbitrary.

The present invention further provides a composition of matter comprising
at least one ester F obtainable by one of the esterification processes described above,
(meth)acrylic acid and
diluent G.

The composition of matter of the present invention may further comprise
esterification catalyst C in protonated or unprotonated form,
polymerization inhibitor D and also
any solvent E if used in the esterification.

The composition of matter may have been neutralized and have a pH as cited above under f).

When the composition of matter has been neutralized, at least a portion of the (meth)acrylic acid has been converted into their water-soluble alkali metal, alkaline earth metal or ammonium salts.

A preferred composition of matter comprises
ester F in a fraction from 0.1% to 40% by weight, more preferably from 0.5% to 20%, even more preferably from 1% to 10%, especially from 2% to 5% and specifically from 2% to 4% by weight,
monomer M at 0.5-99.9% by weight, more preferably 0.5-50% by weight, even more preferably 1-25%, especially 2-15% and specifically from 3% to 5% by weight,
esterification catalyst C at 0-10% by weight, more preferably 0.02-5%, even more preferably 0.05-2.5% by weight and especially 0.1-1% by weight,
polymerization inhibitor D at 0-5% by weight, more preferably 0.01-1.0%, even more preferably 0.02-0.75%, especially 0.05-0.5% and specifically 0.075-0.25% by weight,
solvent E at 0-10% by weight, more preferably 0-5% by weight, even more preferably 0.05-1.5% by weight and especially 0.1-0.5% by weight, with the proviso that the sum total is always 100% by weight, and also
any diluent G ad 100% by weight.

The reaction mixtures obtainable by the above process and compositions of matter according to the present invention can find use
as a radical crosslinker of water-absorbing hydrogels,
as a starting material for producing polymer dispersions,
as a starting material for producing polyacrylates (except hydrogels),
as a paint raw material or
as a cement additive.

Compositions of matter according to the present invention which are particularly useful as radical crosslinkers of water-absorbing hydrogels have a solubility in distilled water at 25° C. of not less than 0.5% by weight, preferably not less than 1% by weight, more preferably not less than 2% by weight, even more preferably not less than 5% by weight, still more preferably not less than 10% by weight, yet even more preferably not less than 20% by weight and especially not less than 30% by weight.

k) The reaction mixture from the esterification, including workup steps thereof, where practiced, for example the reaction mixture from f) or, when f) is omitted, from b) or, when b) is omitted, the reaction mixture from a), can optionally be admixed with additional monoethylenically unsaturated compounds N which bear no acid groups but are copolymerizable with the hydrophilic monomers M and can then be polymerized in the presence of at least one radical initiator K and optionally at least one grafting base L to prepare water-absorbing hydrogels.

It may be preferable l) to postcrosslink the reaction mixture of k).

Useful hydrophilic monomers M for preparing k) these highly swellable hydrophilic hydrogels include for example acids capable of addition polymerization, such as acrylic acid, methacrylic acid, ethacrylic acid, α-chloroacrylic acid, crotonic acid, maleic acid, maleic anhydride, vinylsulfonic acid, vinylphosphonic acid, maleic acid, maleic anhydride, fumaric acid, itaconic acid, citraconic acid, mesaconic acid, glutaconic acid, aconitic acid, allylsulfonic acid, sulfoethyl acrylate, sulfoethyl methacrylate, sulfopropyl acrylate, sulfopropyl methacrylate, 2-hydroxy-3-acryioyloxypropylsulfonic acid, 2-hydroxy-3-methacryloyloxypropylsulfonic acid, allylphosphonic acid, styrenesulfonic acid, 2-acrylamido-2-methylpropanesulfonic acid, 2-acrylamido-2-methylpropanephosphonic acid and also their amides, hydroxyalkyl esters and amino- or ammonio-containing esters and amides. These monomers can be used alone or mixed with each other. Furthermore water-soluble N-vinylamides and also diallyldimethylammonium chloride. Preferred hydrophilic monomers are compounds of the formula V

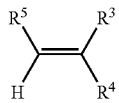

where $R^3$ is hydrogen, methyl or ethyl, $R^4$ is —COOR$^6$, a sulfonyl group, a phosphonyl group, a ($C_1$-$C_4$)-alkanol-esterified phosphonyl group of the formula VI

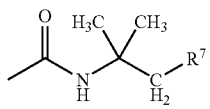

$R^5$ is hydrogen, methyl, ethyl or a carboxyl group, $R^6$ is hydrogen, amino or hydroxy-($C_1$-$C_4$)-alkyl and $R^7$ is a sulfonyl group, a phosphonyl group or a carboxyl group.

Examples of ($C_1$-$C_4$)-alkanols are methanol, ethanol, n-propanol and n-butanol.

Particularly preferred hydrophilic monomers are acrylic acid and methacrylic acid, especially acrylic acid.

To optimize properties, it can be sensible to use additional monoethylenically unsaturated compounds N which do not bear an acid group but are copolymerizable with the monomers bearing acid groups. Such compounds include for example the amides and nitriles of monoethylenically unsaturated carboxylic acid, for example acrylamide, methacrylamide and N-vinylformamide, N-vinylacetamide, N-methylvinyl-acetamide, acrylonitrile and methacrylonitrile. Examples of further suitable compounds are vinyl esters of saturated $C_1$- to $C_4$-carboxylic acids such as vinyl formate, vinyl acetate or vinyl propionate, alkyl vinyl ethers having at least 2 carbon atoms in the alkyl group, for example ethyl vinyl ether or butyl vinyl ether, esters of monoethylenically unsaturated $C_3$- to $C_6$-carboxylic acids, for example esters of monohydric $C_1$- to $C_{18}$-alcohols and acrylic acid, methacrylic acid or maleic acid, monoesters of maleic acid, for example methyl hydrogen maleate, N-vinyllactams such as N-vinylpyrrolidone or N-vinylcaprolactam, acrylic and methacrylic esters of alkoxylated monohydric saturated alcohols, for example of alcohols having from 10 to 25 carbon atoms which have been reacted with from 2 to 200 mol of ethylene oxide and/or propylene oxide per mole of alcohol, and also monoacrylic esters and monomethacrylic esters of polyethylene glycol or polypropylene glycol, the molar masses (Mn) of the polyalkylene glycols being up to 2000, for example. Further suitable monomers are styrene and alkyl-substituted styrenes such as ethylstyrene or tert-butylstyrene.

These monomers without acid groups may also be used in mixture with other monomers, for example mixtures of vinyl acetate and 2-hydroxyethyl acrylate in any proportion. These monomers without acid groups are added to the reaction mixture in amounts within the range from 0 to 50% by weight, preferably less than 20% by weight.

The crosslinked (co)polymers preferably consist of acid-functional monoethylenically unsaturated monomers which have optionally been converted into their alkali metal or ammonium salts before or after polymerization and of 0-40% by weight based on their total weight of monoethylenically unsaturated monomers which do not bear acid groups.

The production, testing and use of (meth)acrylic acid (co)polymers, polyacrylic acids and superabsorbents has been extensively described before and therefore is well known, see for example "Modern Superabsorbent Polymer Technology", F. L. Buchholz and A. T. Graham, Wiley-VCH, 1998 or Markus Frank-"Superabsorbents" in Ullmann's Handbuch der technischen Chemie, Volume 35, 2003.

Preference is given to such hydrogels which are obtained by crosslinking addition polymerization or copolymerization of acid-functional monoethylenically unsaturated monomers M or salts thereof.

The polymers obtainable are notable for an improved saponification index (VSI).

In the postcrosslinking process, the starting polymer is treated with a postcrosslinker and preferably during or after the treatment postcrosslinked and dried by raising the temperature, the crosslinker preferably being included in an inert solvent. Inert solvents are solvents which substantially do not react either with the starting polymer or with the postcrosslinker. Preference is given to such solvents which do not react chemically with the starting polymer or with the postcrosslinker to an extent of more than 90%, preferably more than 95%, more preferably more than 99% and especially more than 99.5%.

Postcrosslinking l) and drying m) is preferably carried out at from 30 to 250° C., especially 50-200° C. and most preferably at from 100 to 180° C. The surface postcrosslinking solution is preferably applied by spraying the polymer in suitable spray mixers. After spraying, the polymer powder is thermally dried, and the crosslinking reaction can take place not only before but also during the drying operation. Preference is given to spraying a solution of the crosslinker in reaction mixers or mixing and drying ranges such as for example Lödige mixers, BEPEX mixers, NAUTA mixers, SHUGGI mixers or PROCESSALL. It is moreover also possible to use fluidized bed dryers.

The drying operation can take place in the mixer itself, by heating of the shell or by blowing in hot air. Also suitable is a downstream dryer such as for example a shelf dryer, a rotary tube oven or a heatable screw. But it is also possible to utilize an azeotropic distillation as drying technique, for example. The preferred residence time at this temperature in the reaction mixer or dryer is below 60 min and more preferably below 30 min.

Preference is given to the above processes wherein the starting polymer is a polymeric acrylic acid or a polyacrylate, especially a polymeric acrylic acid or a polyacrylate obtained by free-radical polymerization using a polyfunctional ethylenically unsaturated radical crosslinker.

Preference is given to such processes wherein the composition of matter containing radical crosslinkers, ie the ester F, and diluents G in a ratio of 0.1-20% by weight and especially 0.5-10% by weight based on the mass of the starting polymer is used.

Preference is given to such processes wherein the radical crosslinker is used in a dose of 0.01-5.0% by weight, preferably 0.02-3.0% by weight, more preferably 0.03-2.5% by weight, especially 0.05-1.0% and specifically from 0.1% to 0.75% by weight based on the starting polymer.

The present invention also provides polymers prepared by one of the processes mentioned above and for their use in hygiene articles, packaging materials and nonwovens and also for the use of an abovementioned composition of matter for producing crosslinked or thermally crosslinkable polymers, especially in paints and varnishes.

The highly swellable hydrophilic hydrogels to be used (starting polymers) are in particular polymers of (co)polymerized hydrophilic monomers M, graft (co)polymers of one or more hydrophilic monomers M on a suitable grafting base L, crosslinked cellulose or starch ethers or natural products capable of swelling in aqueous fluids, for example guar derivatives. These hydrogels are known to one skilled in the art and are described for example in U.S. Pat. No. 4,286,082, DE-C-27 06 135, U.S. Pat. No. 4,340,706, DE-C-37 13 601, DE-C-28 40 010, DE-A-43 44 548, DE-A-40 20 780, DE-A-40 15 085, DE-A-39 17 846, DE-A-38 07 289, DE-A-35 33 337, DE-A-35 03 458, DE-A-42 44 548, DE-A-42 19 607, DE-A-40 21 847, DE-A-38 31 261, DE-A-35 11 086, DE-A-31 18 172, DE-A-30 28 043, DE-A-44 18 881, EP-A-0 801 483, EP-A-0 455 985, EP-A-0 467 073, EP-A-0 312 952, EP-A-0 205 874, EP-A-0 499 774, DE-A 26 12 846, DE-A-40 20 780, EP-A-0 20 5674, U.S. Pat. No. 5,145,906, EP-A-0 530 438, EP-A-0 670 073, U.S. Pat. No. 4,057,521, U.S. Pat. No. 4,062,817, U.S. Pat. No. 4,525,527, U.S. Pat. No. 4,295,987, U.S. Pat. No. 5,011,892, U.S. Pat. No. 4,076,663, U.S. Pat. No. 4,931,497. Also of particular suitability are highly swellable hydrogels from a manufacturing operation as described in WO 01/38402 and also highly swellable inorganic/organic hybrid hydrogels as described in DE 198 54 575. The content of the aforementioned patent documents, especially the hydrogels obtained by the processes, is incorporated herein by reference.

Suitable grafting bases L for hydrophilic hydrogels obtainable by graft copolymerization of olefinically unsaturated acids can be of natural or synthetic origin. Examples are starch, cellulose, cellulose derivatives and also other polysaccharides and oligosaccharides, polyalkylene oxides, especially polyethylene oxides and polypropylene oxides, and also hydrophilic polyesters.

The water-absorbing polymer is obtainable by free-radical graft copolymerization of acrylic acid or acrylate onto a water-soluble polymer matrix. Nonlimiting examples of suitable water-soluble polymer matrices are alginates, polyvinyl alcohol and polysaccharides such as starch for example. A graft copolymerization for the purposes of the present invention utilizes a polyfunctional ethylenically unsaturated radical crosslinker.

The water-absorbing polymer can be an organic/inorganic hybrid polymer formed from a polymeric acrylic acid or polyacrylate on the one hand and a silicate, aluminate or aluminosilicate on the other. More particularly, the polymeric acrylic acid or polyacrylate used may be obtained by free-radical polymerization using a polyfunctional ethylenically unsaturated radical crosslinker and formed using a water-soluble silicate or soluble aluminate or mixture thereof.

Preferred hydrogels are in particular polyacrylates, polymethacrylates and also the U.S. Pat. No. 4,931,497, U.S. Pat. No. 5,011,892 and U.S. Pat. No. 5,041,496 graft polymers. Very particularly preferred hydrogels are the kneader polymers described in WO 01/38402 and the polyacrylate-based organic/inorganic hybrid hydrogels described in DE 198 545 75.

The substances prepared according to the present invention, which are useful as radical crosslinkers in hydrogels, can be used alone or in combination with other crosslinkers, for example internal or surface crosslinkers, for example the following:

Suitable crosslinkers are in particular methylenebisacrylamide, methylenebismethacrylamide, esters of unsaturated mono- or polycarboxylic acids with polyols, such as diacrylate or triacrylate, for example butanediol diacrylate, butanediol dimethacrylate, ethylene glycol diacrylate, ethylene glycol dimethacrylate, and also trimethylolpropane triacrylate and allyl compounds such as allyl (meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP-A-0 343 427. Suitable crosslinkers are pentaerythritol triallyl ether, pentaerythritol tetraallyl ether, polyethylene glycol diallyl ether, monoethylene glycol diallyl ether, glycerol diallyl ether, glycerol triallyl ether, polyallyl ethers based on sorbitol and also ethoxylated variants thereof. Particularly preferred crosslinkers further include polyethylene glycol diacrylates, ethoxylated derivatives of trimethylolpropane triacrylate, for example Sartomer SR 9035, and also ethoxylated derivatives of glycerol diacrylate and glycerol triacrylate. It is obviously also possible to use mixtures of the above crosslinkers.

Very particular preference is given to hydrogels prepared using an ester F prepared according to the present invention as a radical crosslinker.

The water-absorbing polymer is preferably a polymeric acrylic acid or a polyacrylate. This water-absorbing polymer can be prepared by a process known from the literature. Preference is given to polymers which contain crosslinking comonomers (0.001-10 mol %), but very particular preference is given to polymers which were obtained by free-radical polymerization and where a polyfunctional ethylenically unsaturated radical crosslinker was used.

The highly swellable hydrophilic-hydrogels are preparable by addition polymerization processes known per se. Preference is given to the addition polymerization in aqueous solution conducted as a gel polymerization. It involves, as stated above, dilute, preferably aqueous and more preferably 15-50% by weight aqueous, solutions of one or more hydrophilic monomers and optionally of a suitable grafting base L being polymerized in the presence of a free radical initiator by utilizing the Trommsdorff-Norrish effect (Makromol. Chem. 1, 169 (1947)) preferably without mechanical mixing. The polymerization reaction may be carried out at from 0° C. to 150° C., and preferably at from 10° C. to 100° C., not only at atmospheric pressure but also at superatmospheric or reduced pressure. Typically, the polymerization can also be carried out in a protective gas atmosphere, preferably under nitrogen. The addition polymerization may be induced using high-energy electromagnetic rays or the customary chemical polymerization initiators K, for example organic peroxides, such as benzoyl peroxide, tert-butyl hydroperoxide, methyl ethyl ketone peroxide, cumene hydroperoxide, azo compounds such as azobisisobutyronitrile and also inorganic peroxy compounds such as $(NH_4)_2S_2O_8$, $K_2S_2O_8$ or $H_2O_2$.

They can if desired be used in combination with reducing agents such as ascorbic acid, sodium hydrogensulfite and iron(II) sulfate or redox systems where the reducing component included is an aliphatic and aromatic sulfinic acid, such as benzenesulfinic acid and toluene sulfinic acid or derivatives thereof, for example Mannich adducts of sulfinic acids, aldehydes and amino compounds, as described in DE-C-1 301 566. The performance properties of the polymers can be further improved by postheating the polymer gels in the temperature range from 50° to 130° C. and preferably from 700 to 100° C. for several hours.

The gels obtained are neutralized to the extent of 0-100 mol %, preferably 25-100 mol % and more preferably 50-85 mol % based on monomer used, for which the customary neutralizing agents can be used, preferably alkali metal hydroxides, alkali metal oxides or the corresponding alkali metal carbonates, but more preferably sodium hydroxide, sodium carbonate and sodium bicarbonate.

Neutralization is typically achieved by mixing the neutralizing agent as an aqueous solution or else preferably as a solid into the gel. For this, the gel is mechanically comminuted, for example by means of a meat grinder, and the neutralizing agent is sprayed on, scattered on or poured on and then carefully mixed in. The gel mass obtained can then be repeatedly passed through the meat grinder for homogenization. The neutralized gel mass is then dried with a belt or can dryer until the residual moisture content is preferably below 10% by weight and especially below 5% by weight.

The addition polymerization as such can also be carried out by any other process described in the literature. More particularly, the neutralization of the acrylic acid can also be carried out prior to the polymerization, as described above in step f). The polymerization can then be carried out in a conventional belt reactor or a kneading reactor continuously or else batchwise. When the polymerization is carried out in a belt reactor, initiation by electromagnetic radiation and preferably by UV radiation or alternatively initiation by means of a redox initiator system is particularly preferred. Very particular preference is also given to a combination of the two methods of initiation: electromagnetic radiation and chemical redox initiator system simultaneously.

n) The dried hydrogel can then be ground and sieved, in which case it is customary to use roll mills, pin mills or vibratory mills for the grinding. The preferred particle size of the sieved hydrogel is preferably in the range 45-1000 µm, more preferably at 45-850 µm, even more preferably at 200-850 µm, and most preferably at 300-850 µm, and particular preference is also given to the range from 150 to 850 µm, and very particularly to the range from 150 to 700 µm. These ranges preferably cover 80% by weight of the particles and especially 90% by weight of the particles. The size distribution can be determined using established laser methods.

The present invention further provides crosslinked hydrogels which contain at least one hydrophilic monomer M in copolymerized form and have been crosslinked using an ester F of alkoxylated trimethyolpropane with (meth)acrylic acid. The ester can be prepared in a manner according to the present invention or in a prior art manner and is preferably prepared in a manner according to the present invention.

Useful esters F include compounds as described above.

The CRC value [g/g] of the hydrogel-forming polymers according to the present invention can be measured by the methods indicated in the description and is preferably above 15, especially 16, 18, 20, 22, 24, or higher, more preferably 25, especially 26, 27, 28, 29, even more preferably 30, 31, 32, 33, 34, 35, 36, 37 or higher.

The AUL 0.7 psi value [g/g] of the hydrogel-forming polymers according to the present invention can be measured by the methods indicated in the description part and is preferably above 8, especially 9, 10, 11, 12, 13, 14 or higher, more preferably 15, especially 16, 17, 18, 19, or higher, even more preferably above 20, especially 21, 22, 23, 24, 25, 26, 27, 28, or higher.

The AUL 0.5 psi value [g/g] of the hydrogel-forming polymers according to the present invention can be measured by the methods indicated in the description part and is preferably above 8, especially 9, 10, 11, 12, 13, 14 or higher, more preferably 15, especially 16, 17, 18, 19, or higher, even more preferably above 20, especially 21, 22, 23, 24, 25, 26, 27, 28, or higher.

The saponification index VSI of the hydrogel-forming polymers according to the present invention can be measured by the methods indicated in the description part and is preferably less than 10, especially 9.5, 9 or 8.5 or lower, more preferably less than 8, especially 7.5, 7, 6.5, 6, 5.5 or lower, even more preferably less than 5, especially 4.4, 4 or lower.

Application and use of the hydrogel-forming polymers according to the present invention The present invention further relates to the use of the abovementioned hydrogel-forming polymers in hygiene articles comprising
(P) a liquid-pervious topsheet
(Q) a liquid-impervious backsheet
(R) a core positioned between (P) and (O) and comprising 10-100% by weight of the hydrogel-forming polymer according to the present invention 0-90% by weight of hydrophilic fiber material
preferably 20-100% by weight of the hydrogel-forming polymer according to the present invention, 0-80% by weight of hydrophilic fiber material
more preferably 30-100% by weight of the hydrogel-forming polymer according to the present invention, 0-70% by weight of hydrophilic fiber material
even more preferably 40-100% by weight of the hydrogel-forming polymer according to the present invention, 0-60% by weight of hydrophilic fiber material yet even more preferably 50-100% by weight of the hydrogel-forming polymer according to the present invention, 0-50% by weight of hydrophilic fiber material particularly preferably 60-100% by weight of the hydrogel-forming polymer according to the present invention, 0-40% by weight of hydrophilic fiber material especially preferably 70-100% by weight of the hydrogel-forming polymer according to the present invention, 0-30% by weight of hydrophilic fiber material extremely preferably 80-100% by weight of the hydrogel-forming polymer according to the present invention, 0-20% by weight of hydrophilic fiber material most preferably 90-100% by weight of the hydrogel-forming polymer according to the present invention, 0-10% by weight of hydrophilic fiber material (S) optionally a tissue layer positioned directly above and below said core (R), and (T) optionally an acquisition layer positioned between (P) and (R).

The percentages are to be understood so that in the case of 10-100% by weight, 11%, 12%, 13%, 14%, 15%, 16%, 17%, 18%, 19% up to in each case 100% by weight of hydrogel-forming polymer according to the present invention and all intermediate % (for example 12.2%) are possible and correspondingly hydrophilic fiber material from 0% to in each case 89%, 88%, 87%, 86%, 85%, 83%, 82%, 81% by weight and intermediate percentages (for example 87.8%) are possible. When further materials are present in the core, the percentages of polymer and fiber decrease accordingly. The same applies to the preferred ranges, for example in the case of extremely preferable 81%, 82%, 83%, 84%, 85%, 86%, 87%, 88%, 89% by weight can be present for the hydrogel-forming polymer according to the present invention and correspondingly 19%, 18%, 17%, 16%, 15%, 14%, 13%, 12%, 11% by weight for the fiber material. Thus, 20%, 21%, 22%, 23%, 24%, 25%, 26%, 27%, 28%, 29% to 100% by weight of the hydrogel-forming polymer according to the present invention can be present in the preferred range, 30%, 31%, 32%, 33%, 34%, 35%, 36%, 37%, 38%, 39% to 100% by weight can be present for the hydrogel-forming polymer according to the present invention, in the more preferred range, 40%, 41%, 42%, 43%, 44%, 45%, 46%, 47%, 48%, 49% to 100% by weight can be present for the hydrogel-forming polymer according to the present invention, in the even more preferred range, 50%, 51%, 52%, 53%, 54%, 55%, 56%, 57%, 58%, 59% to 100% by weight can be present for the hydrogel-forming polymer according to the present invention, in the yet even more preferred range, 60%, 61%, 62%, 63%, 64%, 65%, 66%, 67%, 68%, 69% to 100% by weight can be present for the hydrogel-forming polymer according to the present invention, in the particularly preferred range, 70%, 71%, 71%, 72%, 73%, 74%, 75%, 76%, 77%, 78%, 79% to 100% by weight can be present for the hydrogel-forming polymer according to the present invention in the especially preferred range, and 90%, 91%, 92%, 93%, 94%, 95%, 96%, 97%, 98%, 99% or 100% by weight can be present for the hydrogel-forming polymer according to the present invention in the most preferred range.

Hygiene articles for the purposes of the present invention include not only incontinence pads and incontinence briefs for adults but also diapers for infants.

The liquid-pervious topsheet (P) is the layer which is in direct contact with the skin of the wearer. Its material comprises customary synthetic or manufactured fibers or films of polyesters, polyolefins, rayon or natural fibers such as cotton. In the case of non-woven materials the fibers are generally joined together by binders such as polyacrylates. Preferred materials are polyesters, rayon and blends thereof, polyethylene and polypropylene. Examples of liquid-pervious layers are described in WO 99/57355 A1, EP 102 388 3 A2.

The liquid-impervious layer (O) is generally a sheet of polyethylene or polypropylene.

The core (R) includes not only the hydrogel-forming polymer according to the present invention but also hydrophilic fiber material. By hydrophilic is meant that aqueous fluids spread quickly over the fiber. The fiber material is usually cellulose, modified cellulose, rayon, polyester such as polyethylene terephthalate. Particular preference is given to cellulose fibers such as pulp. The fibers generally have a diameter of 1-200 μm and preferably 10-100 μm, and also have a minimum length of 1 mm.

Diaper construction and shape is common knowledge and described for example in WO 95/26 209 page 66 line 34 to page 69 line 11, DE 196 04 601 A1, EP-A-0 316 518 and EP-A-0 202 127. Diapers and other hygiene articles are generally also described in WO 00/65084, especially at pages 6-15, WO 00/65348, especially at pages 4-17, WO 00/35502, especially pages 3-9, DE 19737434, WO 98/8439. Hygiene articles for feminine care are described in the following references. The subject hydrogel-forming polymers capable of absorbing aqueous fluids can be used there. Feminine care references: WO 95/24173: Absorption Article for Controlling Odour, WO 91/11977: Body Fluid Odour Control, EP 389023: Absorbent Sanitary Articles, WO 94/25077: Odour Control Material, WO 97/01317: Absorbent Hygienic Article, WO 99/18905, EP 834297, U.S. Pat. No. 5,762,644, U.S. Pat. No. 5,895,381, WO 98/57609, WO 2000/065083, WO 2000/069485, WO 2000/069484, WO 2000/069481, U.S. Pat. No. 6,123,693, EP 1104666, WO 2001/024755, WO 2001/000115, EP 105373, WO 2001/041692, EP 1074233. Tampons are described in the following references: WO 98/48753, WO 98/41179, WO 97/09022, WO 98/46182, WO 98/46181, WO 2001/043679, WO 2001/043680, WO 2000/061052, EP 1108408, WO 2001/033962, DE 200020662, WO 2001/001910, WO 2001/001908, WO 2001/001909, WO 2001/001906, WO 2001/001905, WO 2001/24729. Incontinence articles are described in the following references: Disposable Absorbent Article for Incontinent Individuals: EP 311344 description pages 3-9; Disposable Absorbent Article: EP 850623; Absorbent Article: WO 95/26207; Absorbent Article: EP 894502; Dry-Laid Fibrous Structure: EP 850 616; WO 98/22063; WO 97/49365; EP 903134; EP 887060; EP 887059; EP 887058; EP 887057; EP 887056; EP 931530; WO 99/25284; WO 98/48753. Feminine care and incontinence articles are described in the following references: Catamenial Device: WO 93/22998 description pages 26-33; Absorbent Members for Body Fluids: WO 95/26209 description pages 36-69; Disposable Absorbent Article: WO 98/20916 description pages 13-24; Improved Composite Absorbent Structures: EP 306262 description pages 3-14; Body Waste Absorbent Article: WO 99/45973. These references and the references therein are hereby expressly incorporated herein.

The hydrogel-forming polymers according to the present invention are very useful as absorbents for water and aqueous fluids, so that they may be used with advantage as a water retainer in market gardening, as a filter aid and particularly as an absorbent component in hygiene articles such as diapers, tampons or sanitary napkins.

Incorporation and fixation of the highly swellable hydrogels according to the present invention In addition to the above-described highly swellable hydrogels, the absorbent composition of the present invention includes constructions which include highly swellable hydrogels or to which they are fixed. Any construction is suitable that is capable of accommodating highly swellable hydrogels and of being integrated into the absorption layer. A multiplicity of such compositions is already known and described in detail in the literature. A construction for installing the highly swellable hydrogels can be for example a fiber matrix consisting of a cellulose fiber mixture (air-laid web, wet laid web) or synthetic polymer fibers (meltblown web, spunbonded web) or else of a fiber blend of cellulose fibers and synthetic fibers. Possible fiber materials are detailed in the chapter which follows. The air-laid web process is described for example in WO 98/28 478. Furthermore, open-celled foams or the like may be used to install highly swellable hydrogels.

Alternatively, such a construction can be the result of fusing two individual layers to form one or better a multiplicity of chambers which contain the highly swellable hydrogels. Such a chamber system is described in detail in EP 0 615 736 A1 page 7 lines 26 et seq.

In this case, at least one of the two layers should be water pervious. The second layer may either be water pervious or water impervious. The layer material used may be tissues or other fabric, closed or open-celled foams, perforated films, elastomers or fabrics composed of fiber material. When the absorbent composition consists of a construction of layers, the layer material should have a pore structure whose pore dimensions are small enough to retain the highly swellable hydrogel particles. The above examples of the construction of the absorbent composition also include laminates composed of at least two layers between which the highly swellable hydrogels are installed and fixed.

Generally it is possible to fix hydrogel particles within the absorbent core to improve dry and wet integrity. Dry and wet integrity describes the ability to install highly swellable hydrogels into the absorbent composition in such a way that they withstand external forces not only in the wet but also in the dry state and highly swellable polymer does not dislocate or spill out. The forces referred to are especially mechanical stresses as occur in the course of moving about while wearing the hygiene article or else the weight pressure on the hygiene article in the case of incontinence especially. As to fixation, one skilled in the art knows a multiplicity of possibilities. Examples such as fixation by heat treatment, addition of adhesives, thermoplastics, binder materials are noted in WO 95/26 209 page 37 line 36 to page 41 line 14. The cited passage is thus part of this invention. Methods for enhancing wet strength are also to be found in WO 2000/36216 A1.

Furthermore, the absorbent composition may comprise a base material, for example a polymer film on which the highly swellable hydrogel particles are fixed. The fixing may be effected not only on one side but also on both sides. The base material can be water pervious or water impervious.

The above constructions of the absorbent composition incorporate the highly swellable hydrogels at a weight fraction of from 10-100% by weight, preferably 20-100% by weight, more preferably 30-100% by weight, even more preferably 40-100% by weight, much more preferably 50-100% by weight, particularly preferably 60-100% by weight, especially preferably 70-100% by weight, extremely preferably 80-100% by weight and most preferably 90-100% by weight, based on the total weight of the construction and of the highly swellable hydrogels.

Fiber Materials of the Absorbent Composition

The structure of the present absorbent composition according to the invention may be based on various fiber materials, which are used as a fiber network or matrices. The present invention includes not only fibers of natural origin (modified or unmodified) but also synthetic fibers.

A detailed overview of examples of fibers which can be used in the present invention is given in WO 95/26 209 page 28 line 9 to page 36 line 8. The cited passage is thus part of this invention.

Examples of cellulose fibers include cellulose fibers which are customarily used in absorption products, such as fluff pulp and cellulose of the cotton type. The materials (soft- or hardwoods), production processes such as chemical pulp, semichemical pulp, chemothermomechanical pulp (CTMP) and bleaching processes are not particularly restricted. For instance, natural cellulose fibers such as cotton, flax, silk, wool, jute, ethylcellulose and cellulose acetate are used.

Suitable synthetic fibers are produced from polyvinyl chloride, polyvinyl fluoride, polytetrafluoroethylene, polyvinylidene chloride, polyacrylic compounds such as ORLON®, polyvinyl acetate, polyethyl vinyl acetate, soluble or insoluble polyvinyl alcohol. Examples of synthetic fibers include thermoplastic polyolefin fibers, such as polyethylene fibers (PULPEX®), polypropylene fibers and polyethylene-polypropylene bicomponent fibers, polyester fibers, such as polyethylene terephthalate fibers (DACRON® or KODEL®), copolyesters, polyvinyl acetate, polyethyl vinyl acetate, polyvinyl chloride, polyvinylidene chloride, polyacrylics, polyamides, copolyamides, polystyrene and copolymers of the aforementioned polymers and also bicomponent fibers composed of polyethylene terephthalate-polyethylene-isophthalate copolymer, polyethyl vinyl acetate/polypropylene, polyethylene/polyester, polypropylene/polyester, copolyester/polyester, polyamide fibers (nylon), polyurethane fibers, polystyrene fibers and polyacrylonitrile fibers. Preference is given to polyolefin fibers, polyester fibers and their bicomponent fibers. Preference is further given to thermally adhesive bicomponent fibers composed of polyolefin of the core-sheath type and side-by-side type on account of their excellent dimensional stability following fluid absorption.

The synthetic fibers mentioned are preferably used in combination with thermoplastic fibers. In the course of the heat treatment, the latter migrate to some extent into the matrix of the fiber material present and so constitute bond sites and renewed stiffening elements on cooling. Additionally the addition of thermoplastic fibers means that there is an increase in the present pore dimensions after the heat treatment has taken place. This makes it possible, by continuous addition of thermoplastic fibers during the formation of the absorbent layer, to continuously increase the fraction of thermoplastic fibers in the direction of the topsheet, which results in a similarly continuous increase in the pore sizes. Thermoplastic fibers can be formed from a multiplicity of thermoplastic polymers which have a melting point of less than 190° C., preferably in the range from 75° C. to 175° C. These temperatures are too low for damage to the cellulose fibers to be likely.

Lengths and diameters of the above-described synthetic fibers are not particularly restricted, and generally any fiber from 1 to 200 mm in length and from 0.1 to 100 denier (gram per 9000 meters) in diameter may preferably be used.

Preferred thermoplastic fibers are from 3 to 50 mm in length, particularly preferred thermoplastic fibers are from 6 to 12 mm in length. The preferred diameter for the thermoplastic fiber is in the range from 1.4 to 10 decitex, and the range from 1.7 to 3.3 decitex (gram per 10 000 meters) is particularly preferred. The form of the fiber may vary; examples include woven types, narrow cylindrical types, cut/chopped yarn types, staple fiber types and continuous filament fiber types.

The fibers in the absorbent composition of the present invention can be hydrophilic and/or hydrophobic. According to the definition of Robert F. Gould in the 1964 American Chemical Society publication "Contact angle, wettability and adhesion", a fiber is referred to as hydrophilic when the contact angle between the liquid and the fiber (or the fiber surface) is less than 90° or when the liquid tends to spread spontaneously on the same surface. The two processes are generally coexistent. Conversely, a fiber is termed hydrophobic when a contact angle of greater than 90° is formed and no spreading is observed.

Preference is given to using hydrophilic fiber material. Particular preference is given to using fiber material which is weakly hydrophilic on the body side and most hydrophilic in the region surrounding the highly swellable hydrogels. In the manufacturing process, layers having different hydrophilicities are used to create a gradient which channels impinging fluid to the hydrogel, where it is ultimately absorbed.

Suitable hydrophilic fibers for use in the absorbent composition of the present invention include for example cellulose fibers, modified cellulose fibers, rayon, polyester fibers, for example polyethylene terephthalate (DACRON®), and hydrophilic nylon (HYDROFIL®). Suitable hydrophilic fibers may also be obtained by hydrophilicizing hydrophobic fibers, for example the treatment of thermoplastic fibers obtained from polyolefins (e.g. polyethylene or polypropylene, polyamides, polystyrenes, polyurethanes, etc.) with surfactants or silica. However, for cost reasons and ease of availability, cellulosic fibers are preferred.

The highly swellable hydrogel particles are embedded into the fiber material described. This can be done in various ways, for example by using the hydrogel material and the fibers together to create an absorbent layer in the form of a matrix, or by incorporating highly swellable hydrogels into fiber mixture layers, where they are ultimately fixed, whether by means of adhesive or lamination of the layers.

The fluid-acquiring and -distributing fiber matrix may comprise synthetic fiber or cellulosic fiber or a mixture of synthetic fiber and cellulosic fiber, in which case the mixing ratio may vary from (100 to 0) synthetic fiber: (0 to 100) cellulosic fiber. The cellulosic fibers used may additionally have been chemically stiffened to increase the dimensional stability of the hygiene article.

The chemical stiffening of cellulosic fibers may be provided in different ways. A first way of providing fiber stiffening is by adding suitable coatings to the fiber material. Such additives include for example polyamide-epichlorohydrin coatings (Kymene® 557H, Hercoles, Inc. Wilmington, Del., USA), polyacrylamide coatings (described in U.S. Pat. No. 3,556,932 or as the Parez® 631 NC commercial product from American Cyanamid Co., Stamford, Conn., USA), melamine-formaldehyde coatings and polyethyleneimine coatings.

Cellulosic fibers may also be chemically stiffened by chemical reaction. For instance, suitable crosslinker substances may be added to effect crosslinking taking place within the fiber. Suitable crosslinker substances are typical substances used for crosslinking monomers including but not limited to $C_2$-$C_8$-dialdehydes, $C_2$-$C_8$-monoaldehydes having acid functionality and in particular $C_2$-$C_9$-polycarboxylic acids. Specific substances from this series are for example glutaraldehyde, glyoxal, glyoxylic acid, formaldehyde and citric acid. These substances react with at least 2 hydroxyl groups within any one cellulose chain or between two adjacent cellulose chains within any one cellulose fiber. The crosslinking causes a stiffening of the fibers, to which greater dimensional stability is imparted as a result of this treatment. In addition to their hydrophilic character, these fibers exhibit uniform combinations of stiffening and elasticity. This physical property makes it possible to retain the capillary structure even under simultaneous contact with fluid and compressive forces and to prevent premature collapse.

Chemically crosslinked cellulose fibers are known and described in WO 91/11162, U.S. Pat. No. 3,224,926, U.S. Pat. No. 3,440,135, U.S. Pat. No. 3,932,209, U.S. Pat. No. 4,035,147, U.S. Pat. No. 4,822,453, U.S. Pat. No. 4,888,093, U.S. Pat. No. 4,898,642 and U.S. Pat. No. 5,137,537. The chemical crosslinking imparts stiffening to the fiber material, which is ultimately reflected in improved dimensional stability for the hygiene article as a whole. The individual layers are joined together by methods known to one skilled in the art, for example intermelting by heat treatment, addition of hot-melt adhesives, latex binders, etc.

Methods of Making the Absorbent Composition

The absorbent composition is composed of constructions which contain highly swellable hydrogels and the highly swellable hydrogels which are present in said constructions or fixed thereto.

Examples of processes to obtain an absorbent composition comprising for example a base material to which highly swellable hydrogels are fixed on one or both sides are known and included by the invention but not limited thereto.

Examples of processes to obtain an absorbent composition comprising for example a fiber material blend of synthetic fibers (a) and cellulose fibers (b) embedded in highly swellable hydrogels (c), the blend ratio varying from (100 to 0) synthetic fiber: (0 to 100) cellulose fiber, include (1) a process where (a), (b) and (c) are mixed together at one and the same time, (2) a process where a mixture of (a) and (b) is mixed into (c), (3) a process where a mixture of (b) and (c) is mixed with (a), (4) a process where a mixture of (a) and (c) is mixed into (b), (5) a process where (b) and (c) are mixed and (a) is continuously metered in, (6) a process where (a) and (c) are mixed and (b) is continuously metered in, and (7) a process where (b) and (c) are mixed separately into (a). Of these examples, processes (1) and (5) are preferred. The apparatus used in this process is not particularly restricted and any customary apparatus known to one skilled in the art can be used.

The absorbent composition obtained in this way can optionally be subjected to a heat treatment, so that an absorption layer having excellent dimensional stability in the moist state is obtained. The heat treatment process is not particularly restricted. Examples include heat treatment by feeding hot air or infrared irradiation. The temperature of the heat treatment is in the range from 60° C. to 230° C., preferably from 100° C. to 200° C., particularly preferably from 100° C. to 180° C.

The duration of the heat treatment depends on the type of synthetic fiber, its amount and the hygiene article production rate. Generally the duration of the heat treatment is in the range from 0.5 second to 3 minutes, preferably from 1 second to 1 minute.

The absorbent composition is generally provided for example with a liquid-pervious topsheet and a liquid-impervious backsheet. Furthermore, leg cuffs and adhesive tabs are attached to finalize the hygiene article. The materials and types of pervious topsheet and impervious backsheet and of the leg cuffs and adhesive tabs are known to one skilled in the art and are not particularly restricted. Examples thereof may be found in WO 95/26 209.

The present invention is advantageous in that the esters F, which are useful as crosslinkers, do not have to be purified after they have been formed and particularly in that the (meth)acrylic acid, preferably acrylic acid, does not have to be removed, since it is generally a monomer for forming the hydrogels.

Experimental Part

Parts per million and percentages are by weight, unless otherwise stated.

The example which follows illustrates the process of the present invention.

EXAMPLES

Production of Crude Acrylate Esters Useful as SAP-Crosslinkers

SAP-crosslinkers are prepared in the examples by esterifying alkoxylated trimethylolpropane with acrylic acid by removing water in an azeotropic distillation. The esterification catalyst in the examples is sulfuric acid. The reactants are introduced in the examples as initial charge in methylcyclohexane entrainer together with a stabilizer mixture consisting of hydroquinone monomethyl ether, triphenyl phosphite and hypophosphorous acid. The reaction mixture is then heated to about 98° C. until the azeotropic distillation starts. During the azeotropic distillation, the temperature in the reaction mixture rises. The amount of water removed is determined. The distillation is discontinued once at least the theoretical amount of water has been removed. Subsequently the entrainer is removed in a vacuum distillation. The product is cooled and used as a crosslinker in SAP production.

Conversion and yield of the reaction is not precisely determined because the water removed in the esterification also contains acrylic acid and acrylic acid is also removed during the vacuum distillation of the entrainer. Similarly, the crude ester still contains free acrylic acid which is titrated together with the catalyst (acid number).

Parts are by weight, unless otherwise stated.

Production of Ester

Acid numbers were determined in accordance with DIN EN 3682.

Example 1

Preparation of Alkoxylated Trimethylolpropane 77 g of trimethylolpropane are placed with 0.5 g of KOH 45% in water as an initial charge in an autoclave and dewatered at 80° C. and reduced pressure (about 20 mbar). 167 g of propylene oxide are then added at 120 to 130° C. and allowed to react at this temperature under elevated pressure. The reaction has ended when no further change in pressure is observed. The reaction mixture is then stirred for a further 30 min at about 120° C. 379 g of ethylene oxide is subsequently added at 145 to 155° C. at elevated pressure over a prolonged period and likewise allowed to react. After purging with inert gas and cooling down to 60° C., the catalyst is separated off by addition of sodium pyrophosphate and subsequent filtration.

Example 2

Preparation of Acrylic Ester 887 parts of approximately 5-tuply propoxylated and 15-tuply ethoxylated trimethylolpropane (as per example 1) is esterified with 216 parts of acrylic acid and 5 parts of sulfuric acid in 345 parts of methylcyclohexane. The assistants used were 3 parts of hydroquinone monomethyl ether, 1 part of triphenyl phosphite and 1 part of hypophosphorous acid. 44 parts of water were removed before the entrainer was removed by vacuum distillation. The product was purified through K300 filter. The acid number is determined. The viscosity is adjusted by addition of 96 parts of acrylic acid. The viscosity of the almost colorless product (iodine color number 0-1) is about 320 mPas.

Making of Hydrogels

To determine the quality of surface crosslinking, the dried hydrogel can be investigated using the following test methods.

Test Methods a) Centrifuge Retention Capacity (CRC)

This method measures the free swellability of the hydrogel in a teabag. 0.2000*0.0050 g of dried hydrogel (particle size fraction 106-850 μm) are weighed into a teabag 60×85 mm in size which is subsequently sealed. The teabag is placed for 30 minutes in an excess of 0.9% by weight sodium chloride solution (at least 0.83 l of sodium chloride solution/1 g of polymer powder). The teabag is then centrifuged for 3 minutes at 250 g. The amount of liquid is determined by weighing back the centrifuged teabag.

b) Absorbency Under Load (AUL) (0.7 psi)

The measuring cell for determining AUL 0.7 psi is a Plexiglass cylinder 60 mm in internal diameter and 50 mm in height. Adhesively attached to its underside is a stainless steel sieve bottom having a mesh size of 36 μm. The measuring cell further includes a plastic plate having a diameter of 59 mm and a weight which can be placed in the measuring cell together with the plastic plate. The plastic plate and the weight together weigh 1345 g. AUL 0.7 psi is determined by determining the weight of the empty Plexiglass cylinder and of the plastic plate and recording it as $W_0$. 0.900*0.005 g of hydrogel-forming polymer (particle size distribution 150-800 μm) is then weighed into the Plexiglass cylinder and distributed very uniformly over the stainless steel sieve bottom. The plastic plate is then carefully placed in the Plexiglass cylinder, the entire unit is weighed and the weight is recorded as $W_a$. The weight is then placed on the plastic plate in the Plexiglass cylinder. A ceramic filter plate 120 mm in diameter and 0 in porosity is then placed in the middle of a Petri dish 200 mm in diameter and 30 mm in height and sufficient 0.9% by weight sodium chloride solution his introduced for the surface of the liquid to be level with the filter plate surface without the surface of the filter plate being wetted. A round filter paper 90 mm in diameter and <20 μm in pore size (S&S 589 Schwarzband from Schleicher & Schüll) is subsequently placed on the ceramic plate. The Plexiglass cylinder containing hydrogel-forming polymer is then placed with plastic plate and weight on top of the filter paper and left there for 60 minutes. At the end of this period, the complete unit is removed from the filter paper and the Petri dish and subsequently the weight is removed from the Plexiglass cylinder. The Plexiglass cylinder containing swollen hydrogel is weighed together with the plastic plate and the weight recorded as $W_b$.

AUL was calculated by the following equation:

$$AUL\ 0.7psi\ [g/g] = [W_b - W_a]/[W_a - W_0]$$

AUL 0.5 psi is measured in similar fashion at a lower pressure.

c) The 16 h Extractables Value is Determined Similarly to the Description in EP-A1 811 636 at Page 13 Line 1 to Line 19.

d) Method for Determining Residual Levels of Crosslinkers in Hydrogels

To determine the level of residual, unconverted crosslinker, this residual crosslinker is initially extracted from the dried hydrogel by a double extraction. To this end, 0.400 g of dry hydrogel and 40 g of 0.9% by weight sodium chloride solution are weighed into a sealable and centrifugable ampoule. 8 ml of dichloromethane are added, the ampoule is sealed and is then shaken for 60 min. The ampoule is thereafter immediately centrifuged at 1500 rpm for 5 min, so that the organic phase is cleanly separated from the aqueous phase.

50 μl of monoethylene glycol are weighed into a second ampoule, about 5-6 ml of the dichloromethane extract are added, the weight of the extract is measured accurately to 0.001 g. The dichloromethane is then evaporated off at 50-55° C. and the residue after cooling is taken up with 2 ml of methanol-water mixture (50 parts by volume of each). This is followed by shaking for 10 min before filtration through a PTFE 0.45 μm filter.

The sample thus obtained is separated by means of liquid phase chromatography and analyzed by mass spectrometry. Quantification is against a dilution series of the same crosslinker used.

The chromatography column used is a Zorbax Eclipse XDB C-8 (150×4.6 mm-5 μm) and the precolumn used is a Zorbax Eclipse XDB C-8 (12.5×4.6 mm-5 μm). The mobile phase used is a 75/25 methanol/water mixture.

The gradient course is as follows:

| Time (min) | % Methanol | % Water |
|---|---|---|
| 0 | 75 | 25 |
| 3 | 75 | 25 |
| 4 | 98 | 2 |
| 8 | 98 | 2 |
| 9 | 75 | 25 |
| 14 | 75 | 25 |

Flow is 1 ml/min at 1600 psi pressure.
The injection volume is 20 μl.
Typical analysis time is 14 min for the samples.

Detection is by mass spectrometry, for example in the range 800-1300 m/z (full scan, positive). The instrument utilizes APCI (atmospheric pressure chemical ionization, positive ionization). For optimization, the capillary temperature is set to 180° C., the APCI vaporizer temperature to 450° C., source current to 5.0 μA and gas flow to 80 ml/min.

The individual settings have to be done separately for each crosslinker. To this end, a suitable calibrating solution of the crosslinker is used to determine the characteristic peaks which are later relevant for evaluation. The main peak is generally chosen.

The residual crosslinker concentration is then calculated as follows:

$$CONC_{Probe} = A_{Probe} \times CONC_{Std} \times VF/A_{Std}$$

$CONC_{Probe}$: is wanted residual crosslinker concentration in dry hydrogel in mg/kg
$CONC_{Std}$: is wanted residual crosslinker concentration in calibrating solution in mg/kg
$A_{Probe}$: is peak area of extract sample of dried hydrogel
$A_{Std}$: is peak area of calibrating solution
VF is the dilution factor:

$$VF = M_{DCM} \times M_{Solv}/(M_{probe} \times M_{Extract})$$

$M_{DCM}$ is weight of dichloromethane for extraction
$M_{Probe}$ is weight of dry hydrogel
$M_{Solv}$ is weight of methanol-water mixture+monoethylene glycol
$M_{Extract}$ is weight of dichloromethane extract A calibration has to be carried out (involving a plurality of points in the range 0-50 ppm for example) to ensure that the determination is carried out in the linear range.

e) Saponification Index VSI

The comminuted gel is then further treated in two different ways:

Workup Method 1:

The comminuted gel is evenly spread out in a thin layer on sieve-bottomed trays and then dried at 80° C. under reduced pressure for 24 h. This form of drying is very gentle on the product and therefore represents the best standard for comparison.

The dried hydrogel is then ground and the sieve fraction of 300-600 micrometers is isolated.

Workup Method 2:

The comminuted gel is initially heat-treated at 90° C. in a sealed plastic bag for 24 h. It is then spread out evenly in a thin layer on sieve-bottomed trays and dried at 80° C. under reduced pressure for 24 h. This drying simulates the drying conditions which occur in typical manufacturing plants and which customarily limit the drying performance and the throughput because of the reduced quality associated therewith.

The dried hydrogel is ground and the sieve fraction of 300-600 micrometers is isolated.

The hydrogels obtained according to the two workup methods are characterized by determination of teabag capacity (CRC) and also of the extractables content after 16 h and with regard to the level of unreacted, residual crosslinker. In addition, the moisture content is determined and if found to be above 1% by weight it is arithmetically allowed for when determining these properties. Typically, the moisture content will be about 5% by weight.

The measured values are then used to determine the saponification index (VSI) of the crosslinker in the gel, which computes as follows:

$$VSI = 0.5 \times (CRC_2 - CRC_1) + 0.5 \times (extractables_2 - extractables_1)$$

The subscripted indices here indicate workup method 1 and workup method 2, as the case may be. Thus, the saponification index increases when teabag capacity increases as a result of plant drying and when the fraction of extractables increases in the process. The two contributions are given equal weight.

It is generally advantageous to use crosslinkers whose saponification index is very small. The ideal crosslinker has a VSI of zero. The use of such crosslinkers makes it possible to increase the performance of the plant dryers to the technically achievable maximum without loss of quality. The reason for this is that the degree of crosslinking achieved during the polymerization—and hence the properties of the end product—does not change any more by hydrolysis in the course of drying.

Example 3

Preparation of Superabsorbent Using the Acrylic Ester of Example 2 and Other Internal Crosslinkers Example a 305 g of acrylic acid and 3204 g of a 37.3% by weight sodium acrylate solution are dissolved in 1465 g of distilled water in an acid-resistant plastics tub. 12.2 g of TMP 15EO triacrylate are added as a crosslinker and also 0.61 g of V-50 (2,2'-azobis-amidinopropane dihydrochloride) and 3.05 g of sodium persulfate as initiators. The initiators are advantageously predissolved in a portion of the batch water. The batch is thoroughly stirred for some minutes.

Then nitrogen gas is bubbled through the plastics film covered solution in the tub for about 30 min in order that oxygen may be removed and a homogeneous distribution may be achieved for the crosslinker. Finally, 0.244 g of hydrogen peroxide dissolved in 5 g of water and also 0.244 g of ascorbic acid dissolved in 5 g of water are added. The temperature at the start of the reaction should be 11-13° C. The reaction solution is about 6 cm deep. The reaction starts after a few minutes and is allowed to proceed under adiabatic conditions and the thermally insulated tub is allowed to stand thermally for not longer than 30 min before the gel is worked up.

To work up the gel, the gel block is initially broken into pieces and then comminuted through a meat grinder equipped with a 6 mm breaker plate.

The comminuted gel is then further treated in two different ways:

Workup Method 1

The comminuted gel is evenly spread out in a thin layer on sieve-bottomed trays and then dried at 80° C. under reduced pressure for 24 h. This form of drying is very gentle on the product and therefore represents the best standard for comparison.

The dried hydrogel is then ground and the sieve fraction of 300-600 micrometers is isolated.

Workup Method 2:

The comminuted gel is initially heat-treated at 90° C. in a sealed plastic bag for 24 h. It is then spread out evenly in a thin layer on sieve-bottomed trays and dried at 80° C. under reduced pressure for 24 h. This drying simulates the drying conditions which occur in typical manufacturing plants and which customarily limit the drying performance and the throughput because of the reduced quality associated therewith.

The dried hydrogel is ground and the sieve fraction of 300-600 micrometers is isolated.

The following further examples are prepared similarly to example a:

TABLE 1

| Example No. | Crosslinker type | Amount used based on acrylic acid monomer | Amount used in g |
|---|---|---|---|
| a | TMP - 3 EO triacrylate | 1% by weight | 12.2 g |
| b | TMP - 15 EO triacrylate | 1% by weight | 12.2 g |
| c | TMP - 20 EO triacrylate | 1% by weight | 12.2 g |
| d | TMP - 5 PO - 15 EO triacrylate | 1% by weight | 12.2 g |

The properties achieved for these hydrogels are summarized in tab. 2:

| Ex. | | CRC 1 [g/g] | Extractables 16 h 1 [wt %] | Crosslinker residue 1 [ppm] | CRC 2 [g/g] | Extractables 16 h 2 [wt %] | Crosslinker residue 2 [ppm] | VSI |
|---|---|---|---|---|---|---|---|---|
| a | TMP-3 EO | 36.6 | 4.4 | 857 | 70.6 | 44.2 | 1302 | 36.9 |
| b | TMP-15 EO | 29.7 | 2.8 | 51 | 43.1 | 12.6 | 20 | 11.6 |
| c | TMP-20 EO | 30.3 | 2.9 | 29 | 41.1 | 13.1 | 14 | 10.5 |
| d | TMP-5 PO-15 EO | 29.7 | 2.7 | 18 | 38.7 | 11.0 | <10 | 8.7 |

Example 4a

Preparation of a Superabsorbent Using the Acrylic Ester of Example 2

A Lödige VT 5R-MK plowshare kneader (5 l volume) is charged with 388 g of deionized water, 173.5 g of acrylic acid, 2033.2 g of a 37.3% by weight sodium acrylate solution (100 mol % neutralized) and also 5.90 g of the crosslinker trimethylolpropane-5 PO-15 EO triacrylate prepared in example 2. This initial charge is inertized by having nitrogen bubbled through it for 20 minutes. Dilute aqueous solutions of 2.112 g of sodium persulfate, 0.045 g of ascorbic acid and also 0.126 g of hydrogen peroxide are then added to start the reaction at about 23° C. After the reaction has started, the temperature of the heating jacket is controlled to the reaction temperature in the reactor. The crumbly gel eventually obtained is then dried in a circulating air drying cabinet at 160° C. for about 3 h. This is followed by grinding and classifying to 300-850 micrometers. The hydrogel obtained is then surface postcrosslinked.

Example 4b

Similar to example 4a, except that the amount of crosslinker used is raised to 12 g.

Example 5a

Comparative Example

Very similar to example 4a, except that the crosslinker trimethylolpropane-15 EO-5 PO triacrylate is used. The gel obtained is clumpy and has to be comminuted in a meat grinder before drying.

Example 5b

Comparative Example

Similar to example 5a, except that the amount of the crosslinker used is raised to 12 g.

Postcrosslinking:

The dry base polymer powder from examples 4 and 5 is sprayed homogeneously (while stirring) with a solution of 0.10% by weight of ethylene glycol diglycidyl ether (from Nagase, Japan), 3.43% by weight of water and 1.47% by weight of 1,2-propanediol, each percentage being based on polymer used.

The moist powder is then heat treated in a drying cabinet at 150° C. for 60 min. It is then sieved once more at 850 micrometers in order that agglomerates may be removed. The properties of this postcrosslinked polymer are determined.

The properties of the postcrosslinked polymers of examples 4 and 5 and also of further variants are summarized in tab. 3:

| Example | Crosslinker type | Amount used | CRC | AAP 0.3 psi | AAP 0.7 psi |
|---|---|---|---|---|---|
| 4a | TMP-5PO-15EO triacrylate | 5.9 g | 36 | 26 | 16 |
| 5a | TMP-15EO-5PO triacrylate | 5.9 g | 41 | 17 | 10 |
| 4b | TMP-5PO-15EO triacrylate | 12 g | 31 | 33 | 26 |
| 5b | TMP-15EO-5PO triacrylate | 12 g | 37 | 23 | 13 |

Only the crosslinker used in examples 4a and 4b evidently leads to product properties typical of state of the art superabsorbents.

The crosslinker used in 5a and 5b, what is more, only leads to very tough and difficult-to-process gels, which are difficult to prepare in a kneader.

What is claimed is:

1. An ester F of formula I

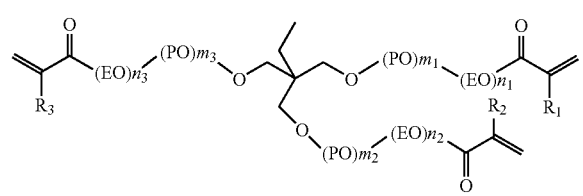

wherein EO is O—CH2-CH2-,
PO is independently at each instance O—CH2-CH(CH3)- or O—CH(CH3)-CH2-,
n1, n2, and n3 are independently 4, 5, or 6,
n1+n2+n3 is 14, 15, or 16,
m1, m2, and m3 are independently 1,2, or 3,
m1+m2+m3 is 4, 5, or 6, and
R1, R2, and R3 are independently H or CH3.

2. The ester F of claim 1 wherein n1+n2+n3 is 15.
3. The ester F of claim 1 wherein n1=n2=n3=5.
4. The ester F of claim 1 wherein m1+m2+m3 is 5.
5. The ester F of claim 1 wherein m1=m2=2 and m3=1.
6. The ester F of claim 1 wherein R1, R2, and R3 are identical.
7. A process for preparing an ester F of claim 1 from an alkoxylated trimethylolpropane of formula II

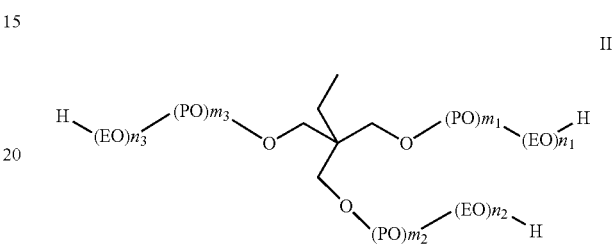

wherein EO, PO, n1, n2, n3, m1, m2, and m3 are each as defined in claim 1, and (meth)acrylic acid, comprising the steps of
a) reacting the alkoxylated trimethyloipropane II with (meth)acrylic acid in the presence of at least one esterification catalyst C, at least one polymerization inhibitor D, and optionally a water-azeotroping solvent E to form the ester F,
b) optionally removing from the reaction mixture some or all of the water formed in a), during and/or after a),
f) optionally neutralizing the reaction mixture,
h) when a solvent E is used, optionally removing the solvent E by distillation, and/or
i) stripping the reaction mixture with a gas which is inert under the reaction conditions,
wherein a molar excess of(meth)acrylic acid to alkoxylated trimethylolpropane in step (a) is at least 3.15:1.
8. The process of claim 7 wherein
the optionally neutralized (meth)acrylic acid present in the reaction mixture after the last process step substantially remains in the reaction mixture.
9. The process of claim 7 wherein the (meth)acrylic acid is not more than 75% by weight removed from the reaction mixture obtained after the last step, which reaction mixture contains the ester F.
10. The process of claim 7 wherein the reaction mixture obtained after the last process step, which contains the ester F, has a DIN EN 3682 acid number of at least 25 mg of KOH/g.
11. The process of claim 7 wherein the reaction mixture obtained after the last process step, which contains the ester F, has a (meth)acrylic acid content of at least 0.5% by weight.
12. The process of claim 7 wherein the molar ratio of (meth)acrylic acid to alkoxylated trimethyloipropane in step a) is at least 15:1.
13. A process for preparing a crosslinked hydrogel comprising the steps of
k) polymerizing an ester F of claim 1 with (meth)acrylic acid, optionally with an additional monoethylenically unsaturated compound N, and optionally at least one further copolymerizable hydrophilic monomer M, in the presence of at least one free-radical initiator K and optionally at least one grafting base L, l) optionally postcrosslinking the reaction mixture obtained from k), m) drying the reaction mixture obtained from k) or l), and n) optionally grinding and/or sieving the reaction mixture obtained from k), l), or m).

14. A process for preparing a crosslinked hydrogel comprising steps a) to i) of claim 7 and additionally k) polymerizing the reaction mixture from one of steps a) to i) of claim 7, if performed, optionally with an additional monoethylenically unsaturated compound N and optionally at least one further copolymerizable hydrophilic monomer M, in the presence of at least one free-radical initiator K and optionally at least one grafting base L, l) optionally postcrosslinking the reaction mixture obtained from k), m) drying the reaction mixture obtained from k) or l), and n) optionally grinding and/or sieving the reaction mixture obtained from k), l), or m).

15. A polymer prepared according to the process of claim 13.

16. A crosslinked hydrogel containing at least one hydrophilic monomer M in polymerized form crosslinked with an ester F of claim 1.

17. A composition comprising from 0.1% to 40% by weight of at least one ester F of claim 1, 0.5-99.9% by weight of at least one hydrophilic monomer M, 0-10% by weight of at least one esterification catalyst C, 0-5% by weight of at least one polymerization inhibitor D, and 0-10% by weight of a solvent E, with the proviso that the sum total is always 100% by weight.

18. The composition of claim 17 further comprising a diluent G.

19. A crosslinked hydrogel prepared from a composition of claim 17, and optionally postcrosslinked.

20. A crosslinked hydrogel having a saponification index of less than 10.

21. A crosslinked hydrogel prepared according to claim 13 having a saponification index of less than 10.

22. The ester F of claim 1 wherein R1, R2, and R3 are H.

23. A polymer prepared according to the process of claim 14.

24. An article comprising a polymer prepared according to the method of claim 13.

25. The article of claim 24 selected from the group consisting of a hygiene article, a packaging material, and a nonwoven.

26. The crosslinked hydrogel of claim 20 having a saponification index of less than 8.

27. The crosslinked hydrogel of claim 21 having a saponification index of less than 9.

* * * * *

UNITED STATES PATENT AND TRADEMARK OFFICE
CERTIFICATE OF CORRECTION

PATENT NO. : 7,259,212 B2 Page 1 of 1
APPLICATION NO. : 10/516698
DATED : August 21, 2007
INVENTOR(S) : Andreas A. Popp et al.

It is certified that error appears in the above-identified patent and that said Letters Patent is hereby corrected as shown below:

On the Title Page:

At field (30), "102 25 943" should be -- 102 25 943.7 --

At field (30), "103 15 336" should be -- 103 15 336.5 --.

In the Claims:

At Column 36, line 28, "trimethyloipropane" should be -- trimethylolpropane --.

At Column 36, line 60, "trimethyloipropane" should be -- trimethylolpropane --.

Signed and Sealed this

First Day of April, 2008

JON W. DUDAS
*Director of the United States Patent and Trademark Office*

UNITED STATES PATENT AND TRADEMARK OFFICE
CERTIFICATE OF CORRECTION

PATENT NO. : 7,259,212 B2
APPLICATION NO. : 10/516698
DATED : August 21, 2007
INVENTOR(S) : Andreas A. Popp et al.

It is certified that error appears in the above-identified patent and that said Letters Patent is hereby corrected as shown below:

On the Title Page:

At field (30), "102 25 943" should be -- 102 25 943.7 --.

At field (30), "103 15 336" should be -- 103 15 336.5 --.

In the Claims:

At Column 36, line 28, "trimethyloipropane" should be -- trimethylolpropane --.

At Column 36, line 60, "trimethyloipropane" should be -- trimethylolpropane --.

Signed and Sealed this

Twenty Second Day of April, 2008

JON W. DUDAS
*Director of the United States Patent and Trademark Office*